(12) United States Patent
Malcolm et al.

(10) Patent No.: US 7,524,831 B2
(45) Date of Patent: Apr. 28, 2009

(54) **TREATMENTS FOR *FLAVIVIRIDAE* VIRUS INFECTION**

(75) Inventors: Bruce A. Malcolm, Westfield, NJ (US); Robert Palermo, New York, NY (US); Xiao Tong, East Brunswick, NJ (US); Boris Feld, New Milford, NJ (US); Hung Le, Rockaway, NJ (US)

(73) Assignee: Schering Corporation, Kenilworth, NJ (US)

( * ) Notice: Subject to any disclaimer, the term of this patent is extended or adjusted under 35 U.S.C. 154(b) by 133 days.

(21) Appl. No.: 11/365,008

(22) Filed: Mar. 1, 2006

(65) Prior Publication Data

US 2006/0198824 A1 Sep. 7, 2006

Related U.S. Application Data

(60) Provisional application No. 60/658,006, filed on Mar. 2, 2005.

(51) Int. Cl.
*A01N 43/04* (2006.01)
*A61K 31/70* (2006.01)

(52) U.S. Cl. ............................. 514/49; 514/42; 514/43; 514/52

(58) Field of Classification Search ........................ None
See application file for complete search history.

(56) References Cited

U.S. PATENT DOCUMENTS

| | | | |
|---|---|---|---|
| 3,853,845 A | 12/1974 | Rousseau et al. | |
| 4,542,021 A | 9/1985 | Kodama et al. | |
| 4,659,825 A | 4/1987 | Holy et al. | |
| 4,812,560 A | 3/1989 | Terada et al. | |
| 4,879,214 A | 11/1989 | Kornher et al. | |
| 4,927,966 A | 5/1990 | Kalman | |
| 5,010,103 A | 4/1991 | Kalman | |
| 5,049,663 A | 9/1991 | Terada et al. | |
| 5,051,498 A | 9/1991 | Kalman | |
| 5,512,298 A | 4/1996 | Aoki et al. | |
| 5,646,269 A | 7/1997 | Matteucci et al. | |
| 5,807,876 A | 9/1998 | Armistead et al. | |
| 5,886,162 A | 3/1999 | Kalman | |
| 5,889,015 A | 3/1999 | Sequeira et al. | |
| 6,147,058 A | 11/2000 | Yoshimura et al. | |
| 6,277,830 B1 | 8/2001 | Ganguly et al. | |
| 6,312,662 B1 | 11/2001 | Erion et al. | |
| 6,316,462 B1 | 11/2001 | Bishop et al. | |
| 6,346,379 B1 | 2/2002 | Gelfand et al. | |
| 6,472,373 B1 | 10/2002 | Albrecht | |
| 6,545,007 B2 | 4/2003 | Sommadossi et al. | |
| 6,566,344 B1 | 5/2003 | Gosselin et al. | |
| 6,599,914 B2 | 7/2003 | Schleimer et al. | |
| 2002/0151536 A1 | 10/2002 | Davis et al. | |
| 2002/0198171 A1 | 12/2002 | Schinazi et al. | |
| 2003/0203872 A1 | 10/2003 | Secrist, III et al. | |
| 2003/0225029 A1 | 12/2003 | Stuyver | |
| 2003/0235582 A1 | 12/2003 | Singh et al. | |
| 2004/0110718 A1 | 6/2004 | Devos et al. | |
| 2004/0265307 A1 | 12/2004 | Singh et al. | |

FOREIGN PATENT DOCUMENTS

| | | |
|---|---|---|
| EP | 0239015 B1 | 10/1991 |
| EP | 0902035 A2 | 3/1999 |
| EP | 0563697 B1 | 7/2001 |
| GB | 1469577 | 4/1977 |
| JP | 52-065281 | 5/1977 |
| JP | 53-141284 | 12/1978 |
| JP | 6-206822 | 7/1994 |
| JP | 6-206822 | 7/2004 |
| WO | WO 94/21658 | 9/1994 |
| WO | WO 95/29930 | 11/1995 |
| WO | WO 99/45016 | 9/1999 |
| WO | WO 00/52015 | 9/2000 |
| WO | WO 01/14345 A1 | 3/2001 |
| WO | WO 01/32153 A2 | 5/2001 |
| WO | WO 01/60315 A2 | 8/2001 |
| WO | WO 01/90121 A2 | 11/2001 |
| WO | WO 01/92282 A2 | 12/2001 |
| WO | WO 01/96353 A2 | 12/2001 |
| WO | WO 02/18404 A2 | 3/2002 |
| WO | WO02/53138 | 7/2002 |
| WO | WO 02/057287 A2 | 7/2002 |
| WO | WO 02/057425 A2 | 7/2002 |
| WO | WO 02/083126 A1 | 10/2002 |
| WO | WO 02/094289 A1 | 11/2002 |
| WO | WO 02/100415 A2 | 12/2002 |
| WO | WO 03/026589 A2 | 4/2003 |
| WO | WO 03/026675 A1 | 4/2003 |
| WO | WO 03/051896 A1 | 6/2003 |
| WO | WO 03/062255 A2 | 7/2003 |

(Continued)

OTHER PUBLICATIONS

Aoshima et al., "Antitumor activities of newly synthesized N4-acyl-1-beta-D-arabinofuranosylcytosine", Cancer Research, vol. 36(8), pp. 2726-2732, 1976.*

(Continued)

*Primary Examiner*—Traviss C McIntosh, III

(57) ABSTRACT

The present invention provides methods for treating infections, in a host, by viruses belonging to the Flaviviridae family, such as HCV, comprising administering an Ara-C homologue to the host.

26 Claims, No Drawings

FOREIGN PATENT DOCUMENTS

| | | |
|---|---|---|
| WO | WO 03/062256 A1 | 7/2003 |
| WO | WO 03/106621 A2 | 12/2003 |
| WO | WO 2004/002422 A2 | 1/2004 |
| WO | WO 2004/046331 A2 | 6/2004 |

OTHER PUBLICATIONS

Johnson, Nucleoside analogues in the treatment of haematological malignancies. Expert Opin Pharmacother. Jun. 2001;2(6):929-43.

Koga et al., Characteristic antitumor activity of cytarabine ocfosfate against human colorectal adenocarcinoma xenografts in nude mice. Cancer Chemother Pharmacol. 1995;36(6):459-62.

Guilhot, The use of interferon-alpha with or without cytarabine and other new agents for the treatment of chronic myeloid leukemia, Fifth Congress of the European Haematology Assn., Birmingham, UK, Jun. 2000, pp. 71-76.

Bartenschlager, in vitro models for hepatitis C. Virus Res. Jan. 30, 2002;82(1-2):25-32.

Bartenschlager, Hepatitis C virus replicons: potential role for drug development. Nat Rev Drug Discov. Nov. 2002;1(11):911-6.

Beisler et al., Synthesis and antitumor activity of dihydro-5-azacytidine, a hydrolytically stable analogue of 5-azacytidine. J Med Chem. Jun. 1977;20(6):806-12.

Bellet et al., Hepatotoxicity of 5-azacytidine (NSC-102816) (a clinical and pathologic study). Neoplasma. 1973;20(3):303-9. No abstract available.

Brachwitz et al., 1-beta-D-Arabinofuranosylcytosine-5'-alkylphosphonophosphates and diphosphates: new orally active derivatives of ara-C. J Lipid Res. Jan. 1998;39(1):162-72.

Braess et al., Oral cytarabine ocfosfate in acute myeloid leukemia and non-Hodgkin's lymphoma—phase I/II studies and pharmacokinetics. Leukemia. Oct. 1998;12(10):1618-26.

Cadman et al., Clinical, biological, and biochemical effects of pyrazofurin. Cancer Res. Mar. 1978;38(3):682-8.

Debernardo et al., Synthesis of oxazinomycin (minimycin). J Org Chem. Jan. 7, 1977;42(1):109-12.

Diamond et al., Mycophenolic acid inhibits dengue virus infection by preventing replication of viral RNA, Virology 304:211-221 (2002).

Dix et al., Pyrazofurin metabolism, enzyme inhibition, and resistance in L5178Y cells, Cancer Res. Nov. 1979;39(11):4485-90.

Endresen et al., Folate supplementation during methotrexate treatment of patients with rehumatoid arthritis. An update and proposals for guidelines. Scan J Rheumatol. 2001;30(3):129-34.

Formann et al., Twice-weekly administration of peginterfereon-alpha-2b improves viral kinetics in patients with chronic hepatitis C genotype 1. J Viral Hepat. Jul. 2003;10(4):271-6.

Hamada et al., Clinical pharmacokinetics of cytarabine formulations. Clin Pharmacokinet. 2002;41(10):705-18.

Harrap et al., Intracellular nucleotide pools and their significance in antimetabolite therapy. Antibiot Chemother. 1980;28:68-77.

Haspel et al., Temperature-sensitive mutants of mouse hepatitis virus produce a high incidence of demyelination. Proc Natl Acad Sci U S A. Aug. 1978;75(8):4033-6.

Higashigawa et al., Deoxyribonucleoside triphosphate pools and Ara-CTP levels in P388 murine leukemic cells treated with 1-B-D-arabinofuranosylcytosine-5'-stearylphosphate which is a newly synthesized derivative of 1-B-D-arabinofuranoslycytosine. Med Oncol Tumor Pharmacother. 1990;7(4):223-6.

Hirota et al., Regioselective BH3-hydride reduction of inosine derivatives, Tetrahedron Letters (2002) 43: 653-655.

Holland et al., Mutation frequencies at defined single codon sites on vesicular stomatitis virus and poliovirus can be increased only slightly by chemical mutagenesis, J. Virol. (1990) 64(8):3960-3962.

Holy, A. et al., A study on hydrolysis of n-dimethylaminomethylenecytidine, -adenosine, -guanosine, and related 2'-deoxy compounds, Oligonucleotidic Compounds. XXXIII, Collection Czecholslov. Chem. Commun. vol. 34 1969:2449-2458.

Imazeki et al., Favorable prognosis of chronic hepatitis C after interferon therapy by long-term cohort study. Hepatology. Aug. 2003;38(2):493-502.

Julias et al., The antiretrovirus drug 3'-azido-3'-deoxythymidine increases the retrovirus mutation rate. J Virol. Jun. 1997;71(6):4254-63.

Kerr et al., Highly water-soluble lipophilic prodrugs of the anti-HIV nucleoside analogue 2-',3'-dideoxycytidine and its 3'-fluoro derivative. J Med Chem. May 29, 1992;35(11):1996-2001.

Kerr et al., N4-(dialkylamino)methylene derivatives of 2'-deoxycytidine and arabinocytidine: physicochemical studies of potential prodrug application. J Pharm Sci. Apr. 1994;83(4):582-6.

Kodama, K. et al., Antitumor activity and pharmacology of 1-beta-D-arabinofuranosylcytosine-5'-stearylphosphate: an orally active derivative of 1-beta-D-arabinofuranoslycytosine. Jpn J Cancer Res. Jul. 1989;80(7):679-85. Erratum in: Jpn J Cancer Res May 1990;81(5):544.

Kreutzer et al., Oxidized, deaminated cytosines are a source of C—>T transitions in vivo. Proc Natl Acad Sci U S A. Mar. 31, 1998;95(7):3578-82.

Krieger et al., Enhancement of hepatitis C virus RNA replication by cell culture-adaptive mutations. J. Virol. May 2001;75(10):4614-24.

Kuhr et al., Treatment of patients with advanced chronic myelogenous leukemia with interferon-alpha-2b and continuous oral cytarabine ocfosfate (YNK01): a pilot study. Leuk Res. Jul. 2000;24(7):583-7.

P.Kong Thoo Lin et al., Synthesis and duplex stability of oligonucleotides containing cytosine-thymine analogues. Nucleic Acids Res. (1985) 17(24): 10373-10383.

Loeb et al., Lethal mutagenesis of HIV by mutagenic ribonucleoside analogs. AIDS Res Hum Retroviruses. Jan. 1, 2000;16(1):1-3.

Loeb et al., Lethal mutagenesis of HIV with mutagenic nucleoside analogs. Proc Natl Acad Sci U S A. Feb. 16, 1999;96(4):1492-7.

Maloisel F. et al., Results of a phase II trial of a combination of oral cytarabine ocfosfate (YNK01) and interferon alpha-2b for the treatment of chronic myelogenous leukemia patients in chronic phase. Leukemia. Apr. 2002;16(4):573-80.

Markland, W. et al., Broad-spectrum antiviral activity of the IMP dehydrogenase inhibitor VX-497: a comparison with ribavirin and demonstration of antiviral additivity with alpha interferon. Antimicrob Agents Chemother. Apr. 2000;44(4):859-66.

McCormick, Patrick J. et al., Changes in ribo- and deoxyribonucleoside triphosphate pools within the cell cycle of a synchronized mouse fibroblast cell line. Biochim Biophys Acta. Mar. 15, 1983;755(1):36-40.

Meyerhans, Andreas et al., Restriction and enhancement of human immunodeficiency virus type 1 replication by modulation of intracellular deoxynucleoside triphosphate pools. J Virol. Jan. 1994;68(1):535-40.

Moriyama, K. et al., Higly efficient random mutagenesis in transcription-reverse-transcription cycles by a hydrogen bond ambivalent nucleoside 5'-triphosphate analogue: potential candidates for a selective anti-retroviral therapy. Nucleosides Nucleotides Nucleic Acids. Aug. 2001;20(8):1473-83.

Neyts, Johan et al., The antiherpesvirus activity of H2G [(R)-9-[4-hydroxy-2-(hydroxymethyl)butyl]guanine] is markedly enhanced by the novel immunosuppressive agent mycophenolate mofetil. Antimicrob Agents Chemother. Dec. 1998;42(12):3285-9.

Pariente, Nonia et al., Efficient virus extinction by combinations of a mutagen and antiviral inhibitors. J Virol. Oct. 2001;75(20):9723-30.

Peasley, K., A nucleoside analogue of 2, 4-difluoropyridine has potential as an antiretroviral agent with multiple and unique mechanisms of action, and may be effective against the HIV organism. Med Hypotheses. Nov. 2000;55(5):408-14.

Grande-Perez, A. et al., Molecular indetermination in the transition to error catastrophe: systematic elimination of lymphocytic choriomeningitis virus through mutagenesis does not correlate linearly with large increases in mutant spectrum complexity. Proc Natl. Acad Sci U S A. Oct. 1, 2002;99(20):12938-43.Epub Sep. 5, 2002.

Resnicoff, Mariana et al., The role of the insulin-like growth factor I receptor in transformation and apoptosis. Ann N Y Acad Sci. Apr. 15, 1998;842:76-81.

Rosti, G. et al., A phase II study of alpha-interferon and oral arabinosyl cytosine (YNK01) in chronic myeloid leukemia. Leukemia. Mar. 2003;17(3):554-9.

Saneyoshi, Mineo et al., Synthetic nucleosides and nucleotides. XVI. Synthesis and biological evaluations of a series of 1-beta-D-arabinofuranosylcytosine 5'-alkyl or arylphosphates. Chem Pharm Bull (Tokyo). Oct. 1980;28(10):2915-23. No abstract available.

Schleyer, E. et al., Pharmacokinetics of Ara-CMP-Sterate (YNK01): phase I study of the oral Ara-C derivative. Leukemia. Jun. 1995;9(6):1085-90.

Sierra, Saleta et al., Response of foot-and-mouth disease virus to increased mutagnesis: influence of viral load and fitness in loss of infectivity. J Virol. Sep. 2000;74(18):8316-23.

Stuyver, Lieven J. et al., Ribonucleoside analogue that blocks replication of bovine viral diarrhea and hepatitis C viruses in culture. Antimicrob Agents Chemother. Jan. 2003;47(1):244-54.

Stuyver, Lieven J. et al., Dynamics of subgenomic hepatitis C virus replicon RNA levels in Huh-7 cells after exposure to nucleoside antimetabolites. J Virol. Oct. 2003;77(19):10689-94.

Traut, Thomas W., Physiological concentrations of purines and pyrimidines. Mol Cell Biochem. Nov. 9, 1994;140(1):1-22. Review.

Ueda, Takanori et al., Clinical pharmacology of 1-beta-D-arabinofuranosylcytosine-5'-stearylphosphate, an orally adminstered long-acting derivative of low-dose 1-beta-D-arabinofluranosylcytosine. Cancer Res. Jan. 1, 1994;54(1):109-13.

Wang, M.C. et al., Studies on the mode of action of 3-deazapyrimidines. 1. Metabolism of 3-deazauridine and 3-deazacytidine in microbial and tumor cells. Biochem Pharmacol. Apr. 15, 1972; 21(8):1063-73. No abstract available.

Whittle, S. L. et al., Folate supplementation and methotrexate treatment in rheumatoid arthritis: a review. Rheumatology (Oxford). Mar. 2004;43(3):267-71. Epub Jan. 6, 2004. Review.

Yi, Minkyung et al., Subgenomic hepatitis C virus replicons inducing expression of a secreted enzymatic report protein. Virology. Dec. 20, 2002; 304(2):197-210.

Ying, C. et al., Ribavirin and mycophenolic acid potentiate the activity of guanine- and diaminopurine-based nucleoside analogues against heptatitis B virus. Antiviral Res. Nov. 2000;48(2):117-24.

Ovokaitys, Todd, Dr. Janet Starr Hull, Ten Steps to Detoxification, Article: Breakthrough in Neglected Essential Nutrition, http://www.detoxprogram.net/articles/issue 13.php. Apr. 6, 2004, 1-29.

Benz, Christopher et al., Modulation of 5-Fluorouracil Cytotoxicity by Intracellular Pools of 5-Phosphoribosyl-1-Pyrophosphate (PRPP), Biochemical Modulation of Anticancer Agents: Experimental and Clinical Approaches, Proceedings of the 18th Annual Detroit Cancer Symposium, Detroit Michigan, USA, Jun. 13-14, 1986, 93-105.

Severson, William E. et al., Ribavirin causes error catastrophe during Hantaan virus replication. J Virol. Jan. 2003;77(1):481-8.

Gahrton, Treatment of acute leukemia—advances in chemotherapy, immunotherapy, and bone marrow transplantation, Adv Cancer Res. 1983;40:255-329.

Inaba et al., [Successful treatment of acute myelogenous leukemia in an elderly patient with cytarabine ocfosfate], Gan To Kagaku Ryoho. Mar. 1994;21(4):535-8. (English Abstract attached).

Keating et al., Improved prospects for long-term survival in adults with acute myelogenous leukemia, Jama. Nov. 19, 1982;248(19):2481-6.

Maloisel et al., Results of a phase II trial of a combination of oral cytarabine ocfosfate (YNK01) and interferon alpha-2b for the treatment of chronic myelogenous leukemia patients in chronic phase, Leukemia. Apr. 2002;16(4):573-80.

Plunkett et al., Cellular pharmacodynamics of anticancer drugs, Semin Oncol. Feb. 1993;20(1):50-63.

* cited by examiner

SEQUENCE LISTING

```
<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: Primer 5B.2F

<400> SEQUENCE: 1
atggacaggc gccctga                                              17

<210> SEQ ID NO 2
<211> LENGTH: 20
<212> TYPE: DNA
<213> ORGANISM: Artificial Sequence
<220> FEATURE:
<223> OTHER INFORMATION: Primer 5B.2R

<400> SEQUENCE: 2
ttgatgggca gcttggtttc                                           20

<210> SEQ ID NO 3
<211> LENGTH: 17
<212> TYPE: DNA
<213> ORGANISM: Artificial Sequence
<220> FEATURE:
<223> OTHER INFORMATION: RT-PCR probe

<400> SEQUENCE: 3
cacgccatgc gctgcgg                                              17
```

TREATMENTS FOR *FLAVIVIRIDAE* VIRUS INFECTION

This application claims the benefit of U.S. provisional patent application No. 60/658,006; filed Mar. 2, 2005 which is herein incorporated by reference in its entirety.

FIELD OF THE INVENTION

The present invention comprises methods for treating or preventing a viral infection in subject.

BACKGROUND OF THE INVENTION

Viruses belonging to the Flaviviridae family include the hepatitis C virus (HCV). The *Flavivirus* genus includes more than 68 members separated into groups on the basis of serological relatedness. Clinical symptoms vary and include fever, encephalitis and hemorrhagic fever. Flaviviruses of global concern that are associated with human disease include the dengue hemorrhagic fever viruses (DHF), yellow fever virus, shock syndrome and Japanese encephalitis virus.

Examples of antiviral agents that have been identified as active against the flavivirus or pestiviruses include:
(1) Interferon and ribavirin;
(2) Substrate-based NS3 protease inhibitors (WO 98/22496);
(3) Non-substrate-based inhibitors such as 2,4,6-trihydroxy-3-nitro-benzamide derivatives (Sudo K. et al., Biochemical and Biophysical Research Communications, 238:643-647 (1997); Sudo K., et al. Antiviral Chemistry and Chemotherapy, 9:186 (1998)), including RD3-4082 and RD3-4078, the former substituted on the amide with a 14 carbon chain and the latter processing a para-phenoxyphenyl group;
(4) Thiazolidine derivatives, which show relevant inhibition in a reverse-phase HPLC assay with an NS3/4A fusion protein and NS5A/5B substrate (Sudo K. et al., Antiviral Research, 32: 9-18 (1996)), especially compound RD-1-6250, possessing a fused cinnamoyl moiety substituted with a long alkyl chain, RD4 6205 and RD4 6193;
(5) Thiazolidines and benzanilides, identified in Kakiuchi N. et al. J. FEBS Letters 421, 217-220; and Takeshita N. et al. Analytical Biochemistry, 247: 242-246 (1997);
(6) A phenanthrenequinone, which possesses activity against protease in a SDS-PAGE and autoradiography assay and is isolated from the fermentation culture broth of *Streptomyces* sp., Sch 68631 (Chu M. et al., Tetrahedron Letters, 37: 7229-7232 (1996)), and Sch 351633, isolated from the fungus *Penicillium griscofuluum*, which demonstrates activity in a scintillation proximity assay;
(7) Selective NS3 inhibitors based on the macromolecule elgin c, isolated from leech (Qasim M. A. et al., Biochemistry, 36: 1598-1607 (1997));
(8) Helicase inhibitors (U.S. Pat. No. 5,633,358);
(9) Polymerase inhibitors, such as nucleotide analogues, gliotoxin (Ferrari E. et al. Journal of Virology, 73:1649-1654 (1999)), and the natural product cerulenin (Lohmann V. et al., Virology, 249: 108-118 (1998));
(10) Antisense phosphorothioate oligodeoxynucleotides (S-ODN) complementary to sequence stretches in the 5' non-coding region (NCR) of the virus, or nucleotides 326-348 comprising the 3' end of the NCR and nucleotides 371-388 located in the core coding region of the HCV RNA;
(11) Inhibitors of IRES-dependent translation;
(12) Nuclease-resistant ribozymes; and
(13) Miscellaneous compounds including 1-amino-alkyloyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3' dideoxyinosine (U.S. Pat. No. 5,026,687 to Yarchoan et al.), and benzimidazoles (U.S. Pat. No. 5,891,874 to Colacino et al.).

Although there are several treatments available for flaviviral infections, some flaviviral infections fail to respond adequately to currently available treatments. Hence, there is a need to provide additional, effective methods for treating and/or preventing such an infection comprising administration of various analogues of Ara-C.

Ara-C an arabinofuranosylcytosine nucleoside analogue, and prodrug analogues of Ara-C, including fosteabine (1-β-D-arabinofuranosylcytosine-5'-stearylphosphate; YNK01), have been used effectively to treat acute myelogenous leukemia and lymphocytic leukemias (Gahrton et al., Adv. Cancer Res. 40:255-329 (1983); Keating et al., JAMA 248:2481-2486 (1982); Plunkett et al., Semin. Oncol. 20:50-63 (1993); Maloisel, et al., Leukemia 16(4): 573-80 (2002); Kuhr et al., Leuk. Res. 24(7): 583-587 (2000); Inaba et al., Gan To Kagaku Ryoho. 21(4): 535-538 (1994)).

Moreover, Ara-C homologues, including $N^4$-(dialkylamino)methylene derivatives of 2'-dC have been shown in the past to be effective in the treatment of infections from retroviruses, including HIV (see e.g., Kerr et al., J. Med. Chem. 35:1996-2001 (1992); Kerr et al., J. Pharm Sci. 83(4): 582-586 and U.S. Pat. No. 5,051,498 and 5,886,162).

This invention addresses the need to identify additional, effective methods for treating or preventing Flaviviridae infections by providing methods using ara-C analogue compounds for the effective treatment or prevention of Flaviviridae virus (e.g., hepatitis C virus) infections.

SUMMARY OF THE INVENTION

The present invention provides a method for (i) treating a host infected with a virus which is a member of the Flaviviridae family of viruses (e.g., hepatitis C virus) or for (ii) preventing infection of a host, with a virus which is a member of the Flaviviridae family of viruses (e.g., hepatitis C virus), for example, following, transplantation of a liver into said host or transfusion of blood into said host, which comprises administering to said host a therapeutically effective amount of a compound of formula I:

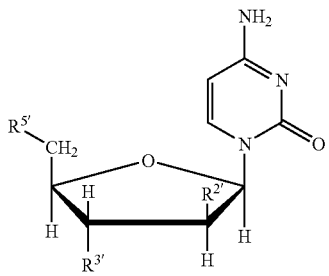

I or a pharmaceutically acceptable salt thereof; wherein $R^{2'}$ and $R^{3'}$ are independently —OH or a pharmaceutically acceptable leaving group which is capable of being converted into —OH, F or —CH$_3$ when the compound represented by formula I is administered in vivo, and $R^{5'}$ is a straight or branched chain $C_9$ to $C_{24}$ alkylphosphate or a straight or branched chain $C_9$ to $C_{24}$ alkenylphosphate group or a pharmaceutically acceptable leaving group which is capable of being converted into —OH or phosphate when the compound represented by formula I is administered in vivo.

In an embodiment of the invention, the compound represented by structural formula I is administered to a host in association with any other anti-viral agent as set forth in the "Pharmaceutical Compositions" section below, for example, an interferon-alfa or a pegylated interferon-alfa; including, but not limited to interferon alfa-2a, interferon alfa-2b, interferon alfa-2c, interferon alfa n-1, interferon alfa n-3, consensus interferon, pegylated interferon alfa-2a, pegylated interferon alfa-2b, pegylated interferon alfa-2c, pegylated interferon alfa n-1, pegylated interferon alfa n-3, pegylated consensus interferon or albumin-interferon-alpha.

In an embodiment, a compound comprising structural formula I is administered to the host in association with ribavirin and/or a pegylated or unpegylated interferon.

Triple combination therapies are also within the scope of the invention wherein a compound represented by structural formula I is administered to a host in association with ribavirin and one or more of the interferons (pegylated or unpegylated) mentioned herein (e.g., pegylated or unpegylated interferon alfa-2a or pegylated or unpegylated interferon alfa-2b).

In an embodiment of the invention, in a compound comprising structural formula I, $R^{2'}=R^{3'}=-$OH; $R^{5'}$ is a $C_{16}$ to $C_{20}$ alkylphosphate group; $R^{5'}$ is a $C_{18}$ to $C_{20}$ alkylphosphate group; $R^{5'}$ is a $C_{18}$ to $C_{20}$ alkenylphosphate group; or $R^{5'}$ is —OPO$_3$H—C$_{18}$H$_{37}$.

The present invention also provides a method for (i) treating a host having hepatitis C virus infection (e.g., chronic infection or acute infection) or for (ii) preventing infection of a host, with hepatitis C virus, for example, following transplantation of a liver into said host or transfusion of blood into said host that comprises administering, to the host, a therapeutically effective amount of a compound represented by structural formula II:

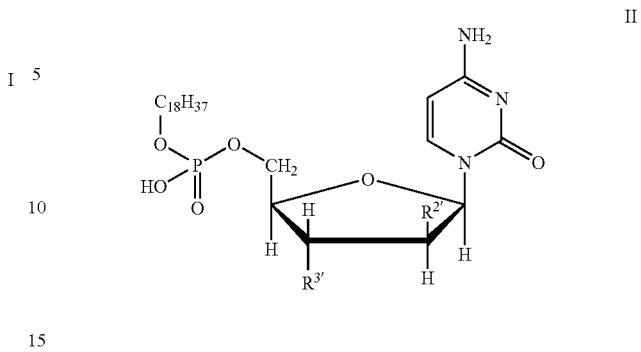

II or a pharmaceutically acceptable salt thereof;

in association with a therapeutically effective amount of an interferon for a treatment time period sufficient to eradicate detectable hepatitic C virus-RNA and to maintain no detectable hepatitis C virus -RNA for at least twelve weeks after the end of the treatment time period; $$$

wherein $R^{2'}$ and $R^{3'}$ are independently —OH or a pharmaceutically acceptable leaving group which is capable of being converted to —OH, F or —CH$_3$ when the compound represented by formula 11 is administered in vivo.

In an embodiment of the invention, a compound represented by structural formula 11 is administered to a host in association with any other anti-viral agent as set forth in the "Pharmaceutical Compositions" section below, for example, pegylated or unpegylated interferon alfa, e.g. selected from the group consisting of pegylated interferon alfa-2a, pegylated interferon alfa-2b, pegylated interferon alfa-2c, pegylated interferon alfa n-1, pegylated interferon alfa n-3, pegylated consensus interferon, interferon alfa-2a, interferon alfa-2b, interferon alfa-2c, interferon alfa n-1, interferon alfa n-3, consensus interferon and albumin-interferon-alpha.

In another embodiment of the invention a compound represented by structural formula 11 is administered to a host in association with ribavirin and/or a pegylated or unpegylated interferon.

Triple combination therapies are also within the scope of the invention wherein a compound represented by structural formula 11 is administered to a host in association with ribavirin and one or more of the interferons (pegylated or unpegylated) mentioned herein (e.g., pegylated or unpegylated interferon alfa-2a or pegylated or unpegylated interferon alfa-2b).

A further embodiment of the invention comprises administering a compound comprising structural formula 11 to a host wherein, in structural formula II, $R^{2'}=R^{3'}=-$OH.

Yet another embodiment of the invention comprises methods wherein the host who is administered a compound comprising a structural formula II is infected with multiple hepatitis C virus genotypes (e.g., genotype 1 and/or genotype 2 and/or genotype 3).

The present invention provides a method for (i) treating a host having hepatitis C virus infection (e.g., chronic infection or acute infection) or for (ii) preventing infection of a host, with hepatitis C virus, for example, following transplantation of a liver into said host or transfusion of blood into said host that comprises administering to the patient a therapeutically effective amount of a compound represented by structural formula III (fosteabine; 1-β-D-arabinofuranosylcytosine-5'-stearylphosphate; YNK01):

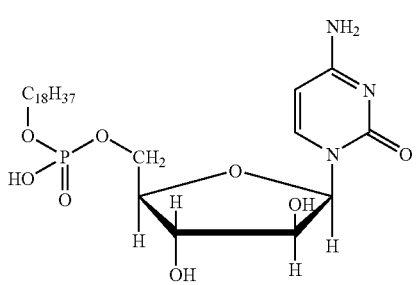

III or a pharmaceutically acceptable salt thereof; optionally in association with a therapeutically effective amount of any other anti-viral agent as set forth in the "Pharmaceutical Compositions" section below, for example, unpegylated or pegylated interferon alfa (e.g., unpegylated or pegylated interferon alfa-2a, unpegylated or pegylated interferon alfa-2b, unpegylated or pegylated interferon alfa-2c, unpegylated or pegylated interferon alfa n-1, unpegylated or pegylated interferon alfa n-3 or unpegylated or pegylated consensus interferon) for a treatment time period sufficient to eradicate detectable hepatitis C virus-RNA and to maintain no detectable hepatitis C virus-RNA for at least twelve weeks after the end of the treatment time period.

In one embodiment of the present invention, the pegylated interferon alfa that is administered to the host in association with a compound represented by structural formula III is a pegylated interferon alfa-2b wherein the amount of pegylated interferon alfa-2b that is administered in the treatment time period is about 0.5 to 1.5 micrograms per kilogram body weight of pegylated interferon alfa-2b protein per week on a weekly basis for at least twenty-four weeks.

In another embodiment of the invention, pegylated interferon alfa that is administered in association with compound represented by structural formula III is a pegylated interferon alfa-2b, wherein the pegylated interferon alfa-2b is administered on a weekly basis for about forty-eight weeks.

Triple combination therapies are also within the scope of the invention wherein a compound represented by structural formula III is administered to a host in association with ribavirin and one or more of the interferons (pegylated or unpegylated) mentioned herein (e.g., pegylated or unpegylated interferon alfa-2a or pegylated or unpegylated interferon alfa-2b).

The present invention provides a method for treating a host infected with a virus which is a member of the Flaviviridae family of viruses (e.g., hepatitis C virus) or for preventing the infection, comprising administering to said host a therapeutically effective amount of a compound represented by formula IV

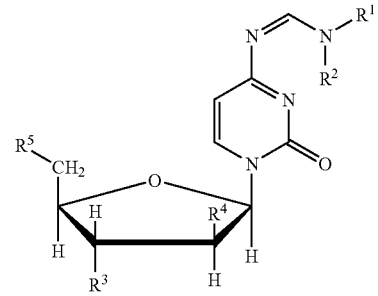

IV or a pharmaceutically acceptable salt thereof; wherein $R^3$ and $R^4$ are independently —OH or a pharmaceutically acceptable leaving group which is capable of being converted to phosphate, —OH, F or —CH$_3$ when the compound represented by formula IV is administered in vivo, wherein $R^5$ is —OH, a straight or branched chain $C_9$ to $C_{24}$ alkylphosphate (e.g., —OPO$_3$—C$_{18}$H$_{37}$) or a straight or branched chain $C_9$ to $C_{24}$ alkenylphosphate group or a pharmaceutically acceptable leaving group which is capable of being converted into —OH, phosphate, F or —CH$_3$ when the compound represented by formula IV is administered in vivo; and wherein $R^1$ and $R^2$ are independently $C_1$ to $C_{10}$ alkyl or wherein $R^1$ and $R^2$ taken together with N form a $C_3$ to $C_7$ ring represented by the following structural formula:

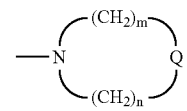

wherein n and m are independently 0, 1, 2 or 3 and Q is CH$_2$, NR, O, S, SO or SO$_2$; and R is independently H, $C_1$ to $C_6$ alkyl or $C_1$ to $C_6$ acyl or wherein $R^1$ and $R^2$, taken together with the N, are represented by the structural formula:

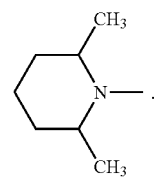

In an embodiment of the invention, the compound represented by structural formula IV is administered in association with interferon-alfa, pegylated interferon-alfa or albumin-interferon-alpha, an interferon-alfa selected from the group consisting of interferon alfa-2a, interferon alfa-2b, interferon alfa-2c, interferon alfa n-1, interferon alfa n-3 and consensus interferon, a pegylated interferon-alfa selected from the group consisting of pegylated interferon alfa-2a, pegylated interferon alfa-2b, pegylated interferon alfa-2c, pegylated interferon alfa n-1, pegylated interferon alfa n-3, or pegylated consensus interferon or any combination thereof.

In an embodiment of the invention, the compound represented by formula IV is further administered in association with ribavirin.

In an embodiment of the invention, in the compound of structural formula IV, $R^3$=$R^4$=$R^5$=—OH; $R^1$ and $R^2$ are $C_1$-$C_5$ alkyl; $R^1$ and $R^2$ are isopropyl; $R^1$ and $R^2$ taken together with N are represented by the structural formula:

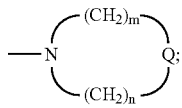

wherein n and m are independently 0, 1, 2 or 3 and Q is $CH_2$, NR, O, S, SO or $SO_2$; and R is independently H, $C_1$ to $C_6$ alkyl or $C_1$ to $C_6$ acyl; or $R^1$ and $R^2$ taken together with N are represented by the following structural formula:

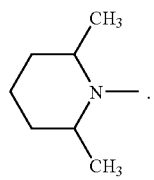

The present invention provides a method for treating a host having a hepatitis C virus infection or for preventing the infection that comprises administering, to the host, a therapeutically effective amount of a compound represented by structural formula V:

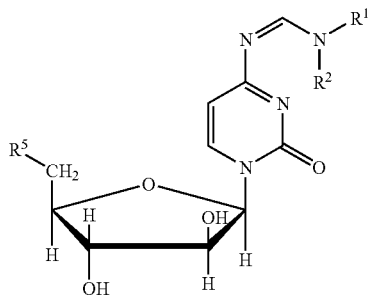

V or a pharmaceutically acceptable salt thereof;
in association with a therapeutically effective amount of an interferon for a treatment time period sufficient to eradicate detectable hepatitic C virus-RNA and to maintain no detectable hepatitic C virus RNA for at least twelve weeks after the end of the treatment time period;
wherein $R^5$ is —OH, a straight or branched chain $C_9$ to $C_{24}$ alkylphosphate (e.g., —$OPO_3$—$C_{18}H_{37}$) or a straight or branched chain $C_9$ to $C_{24}$ alkenylphosphate group or a pharmaceutically acceptable leaving group which is capable of being converted into —OH, phosphate, F or —$CH_3$ when the compound represented by formula V is administered in vivo, and wherein $R^1$ and $R^2$ are independently $C_1$ to $C_{10}$ alkyl or wherein $R^1$ and $R^2$ taken together with N form a $C_3$ to $C_7$ ring represented by the following structural formula:

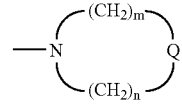

wherein n and m are independently 0, 1, 2 or 3 and Q is $CH_2$, NR, O, S, SO or $SO_2$; and R is independently H, $C_1$ to $C_6$ alkyl or $C_1$ to $C_6$ acyl or wherein $R^1$ and $R^2$, taken together with the N, are represented by the structural formula:

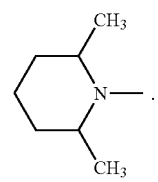

In an embodiment of the invention, the interferon that is administered is pegylated interferon alfa and is selected from the group consisting of pegylated interferon alfa-2a, pegylated interferon alfa-2b, pegylated interferon alfa-2c, pegylated interferon alfa n-1, pegylated interferon alfa n-3, pegylated consensus interferon, interferon alfa-2a, interferon alfa-2b, interferon alfa-2c, interferon alfa n-1, interferon alfa n-3 and consensus interferon.

In an embodiment of the invention, the compound represented by formula V is administered in association with ribavirin. In an embodiment of the invention, $R^5$=—OH.7

In an embodiment of the invention, the host is infected with multiple hepatitis C virus genotypes (e.g., hepatitis C virus genotype 1 and/or hepatitis C virus genotype 2 and/or hepatitis C virus genotype 3).

The present invention provides a method for treating a host having a hepatitis C virus infection or for preventing the infection that comprises administering to the host a therapeutically effective amount of a compound represented by a structural formula selected from the group consisting of:

VI

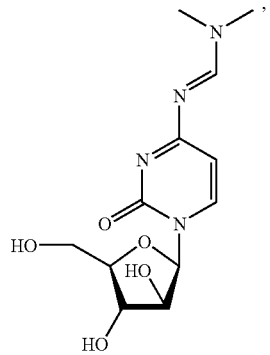

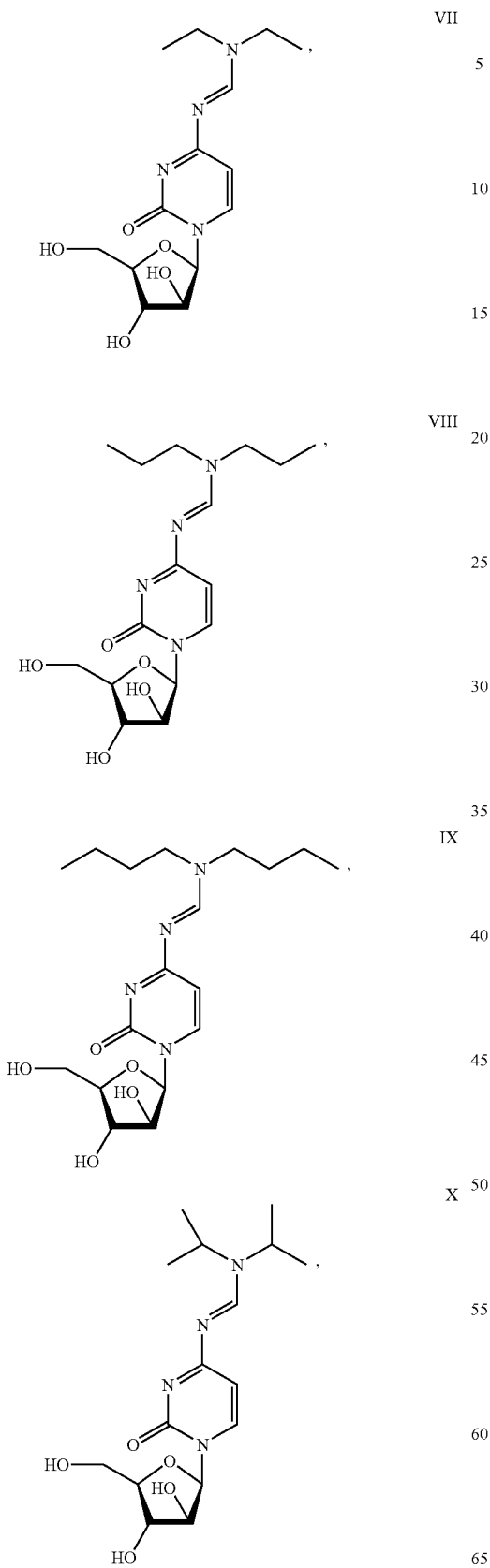
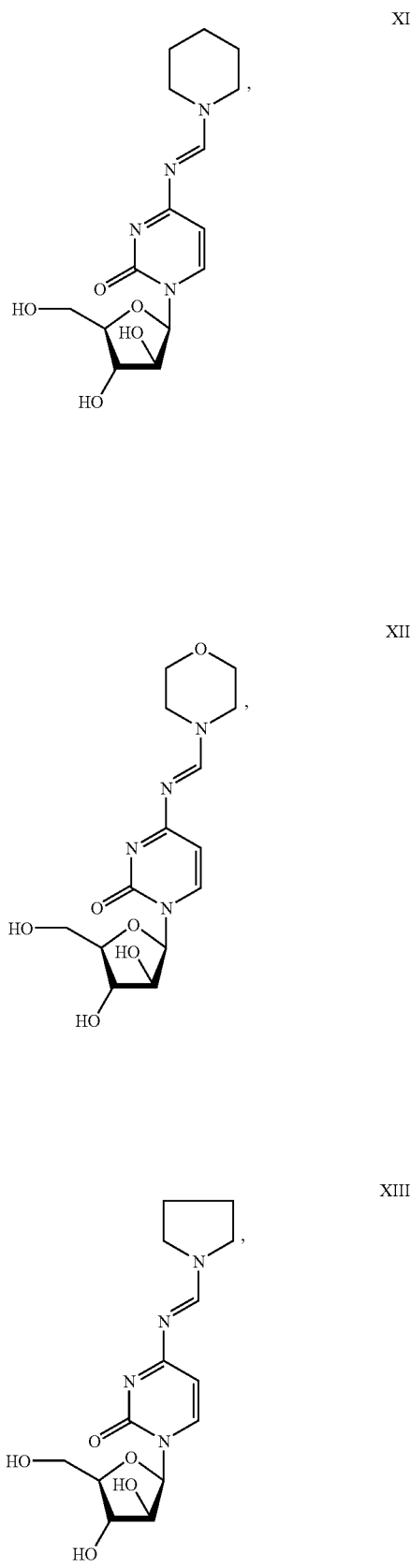

XIV
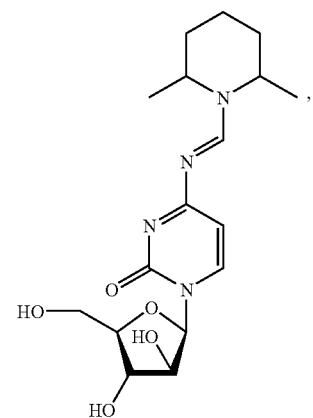
XV
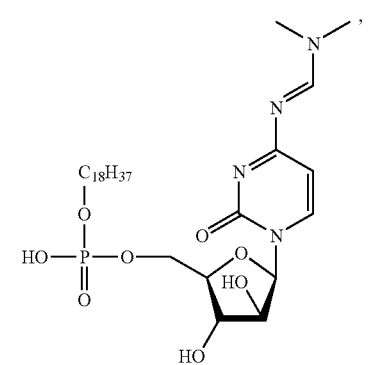
XVI
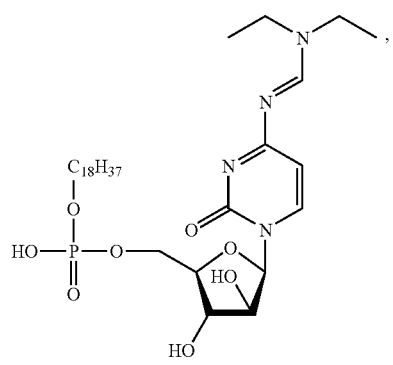
XVII
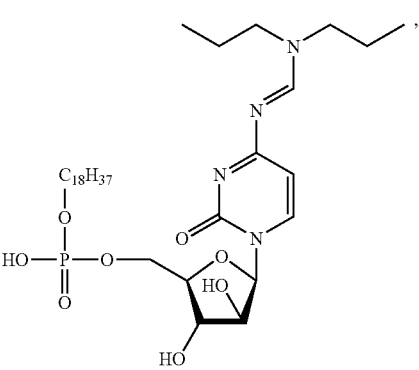
XVIII
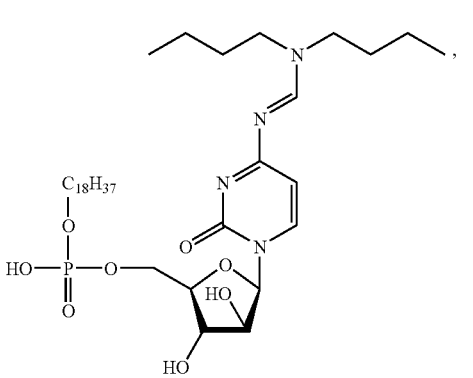
XIX
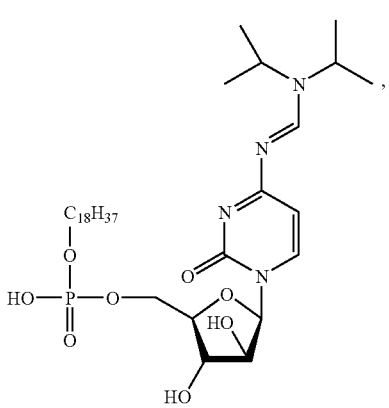
XX
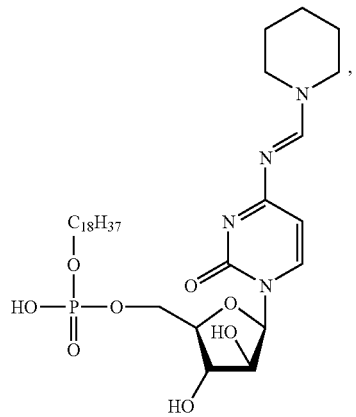
XXI
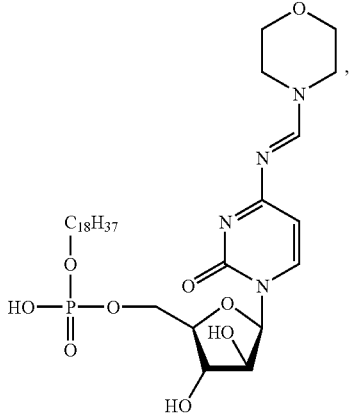

-continued

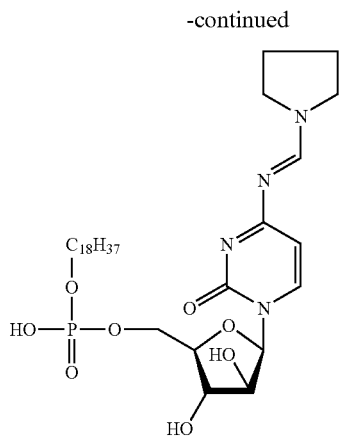

XXII and

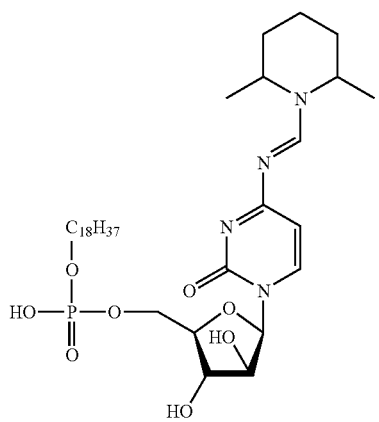

XXIII or a pharmaceutically acceptable salt thereof.

In an embodiment of the invention, a compound selected from structural formulas VI-XXIII is administered to the host in association with any other anti-viral agent as set forth in the "Pharmaceutical Compositions" section below, for example, one or more members selected from the group consisting of pegylated interferon alfa-2a, pegylated interferon alfa-2b, pegylated interferon alfa-2c, pegylated interferon alfa n-1, pegylated interferon alfa n-3, pegylated consensus interferon, interferon alfa-2a, interferon alfa-2b, interferon alfa-2c, interferon alfa n-1, interferon alfa n-3 and consensus interferon.

In an embodiment of the invention, a compound selected from structural formulas VI-XXIII is administered to the host in association ribavirin.

The present invention provides a method for preventing infection of a host, with a virus which is a member of the Flaviviridae family of viruses (e.g., hepatitis C virus), following transplantation of a liver into said host or transfusion of blood into said host or for treating the infection in the host comprising administering to said host a therapeutically effective amount of a compound represented by structural formula IV:

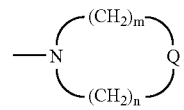

IV or a pharmaceutically acceptable salt thereof; wherein $R^3$ and $R^4$ are independently —OH or a pharmaceutically acceptable leaving group which is capable of being converted to phosphate, —OH, F or —CH$_3$ when the compound represented by formula IV is administered in vivo, wherein $R^5$ is —OH, a straight or branched chain $C_9$ to $C_{24}$ alkylphosphate (e.g., —OPO$_3$—C$_{18}$H$_{37}$) or a straight or branched chain $C_9$ to $C_{24}$ alkenylphosphate group or a pharmaceutically acceptable leaving group which is capable of being converted into —OH, phosphate, F or —CH$_3$ when the compound represented by formula IV is administered in vivo and wherein $R^1$ and $R^2$ are independently $C_1$ to $C_{10}$ alkyl or wherein $R^1$ and $R^2$ taken together with N form a $C_3$ to $C_7$ ring represented by the following structural formula:

$$\begin{array}{c} -N \begin{cases} (CH_2)_m \\ (CH_2)_n \end{cases} Q \end{array}$$

wherein n and m are independently 0, 1, 2 or 3 and Q is CH$_2$, NR, O, S, SO or SO$_2$; and R is independently H, $C_1$ to $C_6$ alkyl or $C_1$ to $C_6$ acyl or wherein $R^1$ and $R^2$, taken together with the N, are represented by the structural formula:

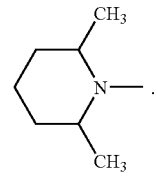

In an embodiment of the invention, the compound represented by formula IV is administered in association with any other anti-viral agent as set forth in the "Pharmaceutical Compositions" section below, for example, interferon-alfa, pegylated interferon-alfa, albumin-interferon-alpha, interferon alfa-2a, interferon alfa-2b, interferon alfa-2c, interferon alfa n-1, interferon alfa n-3, consensus interferon, pegylated interferon alfa-2a, pegylated interferon alfa-2b, pegylated interferon alfa-2c, pegylated interferon alfa n-1, pegylated interferon alfa n-3, or pegylated consensus interferon.

In an embodiment of the invention, the compound represented by formula IV is administered in association with ribavirin.

In an embodiment of the invention, in the compound represented by formula IV: $R^3$=$R^4$=—OH; $R^3$=$R^4$=$R^5$=—

OH; $R^1$ and $R^2$ are $C_1$-$C_5$ alkyl; $R^1$ and $R^2$ are isopropyl; $R^1$ and $R^2$ taken together with N are represented by the structural formula:

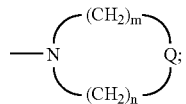

wherein n and m are independently 0, 1, 2 or 3 and Q is $CH_2$, NR, O, S, SO or $SO_2$; and R is independently H, $C_1$ to $C_6$ alkyl or $C_1$ to $C_6$ acyl; or $R^1$ and $R^2$ taken together with N are represented by the following structural formula:

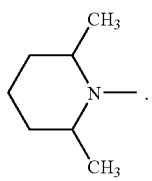

The present invention provides a composition represented by formula IV

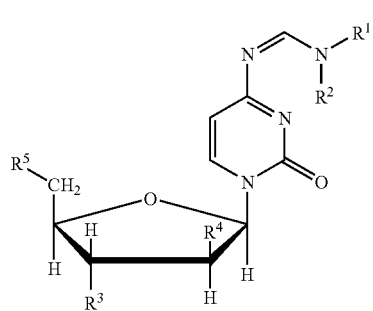

or a pharmaceutically acceptable salt thereof; wherein $R^3$ and $R^4$ are independently —OH or a pharmaceutically acceptable leaving group which is capable of being converted to phosphate, —OH, —F or —$CH_3$ when the compound represented by formula IV is administered in vivo, wherein $R^5$ is —OH, a straight or branched chain $C_9$ to $C_{24}$ alkylphosphate or a straight or branched chain $C_9$ to $C_{24}$ alkenylphosphate group or a pharmaceutically acceptable leaving group which is capable of being converted into —OH, phosphate, F or —$CH_3$ when the compound represented by formula IV is administered in vivo and wherein $R^1$ and $R^2$ are independently $C_1$ to $C_{10}$ alkyl or wherein $R^1$ and $R^2$ taken together with N form a $C_3$ to $C_7$ ring represented by the following structural formula:

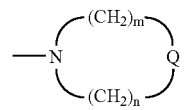

wherein n and m are independently 0, 1, 2 or 3 and Q is $CH_2$, NR, O, S, SO or $SO_2$; and R is independently H, $C_1$ to $C_6$ alkyl or $C_1$ to $C_6$ acyl or wherein $R^1$ and $R^2$, taken together with the N, are represented by the structural formula:

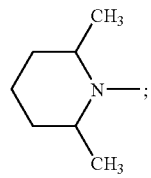

optionally in association with any other anti-viral agent as set forth in the "Pharmaceutical Compositions" section below, for example, one or more members selected from the group consisting of pegylated interferon alfa-2a, pegylated interferon alfa-2b, pegylated interferon alfa-2c, pegylated interferon alfa n-1, pegylated interferon alfa n-3, pegylated consensus interferon, interferon alfa-2a, interferon alfa-2b, interferon alfa-2c, interferon alfa n-1, interferon alfa n-3 and consensus interferon. In an embodiment of the invention, the compound is represented by a structural formula selected from the group consisting of:

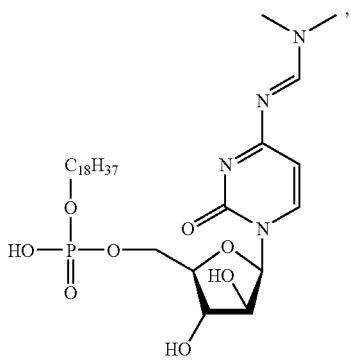

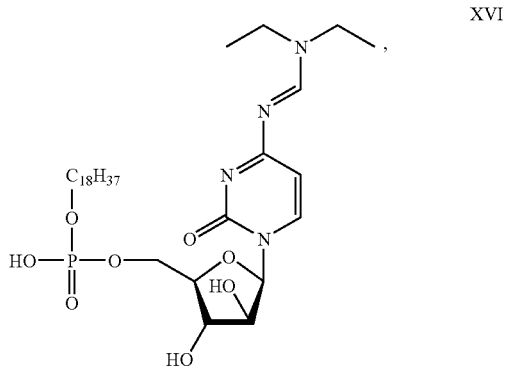

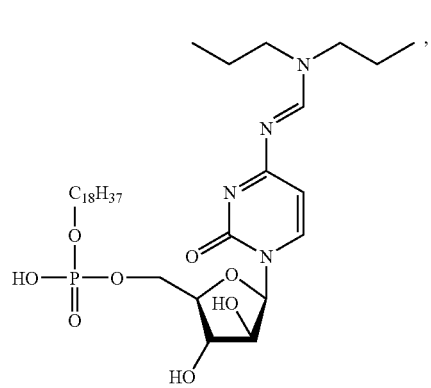
XVII
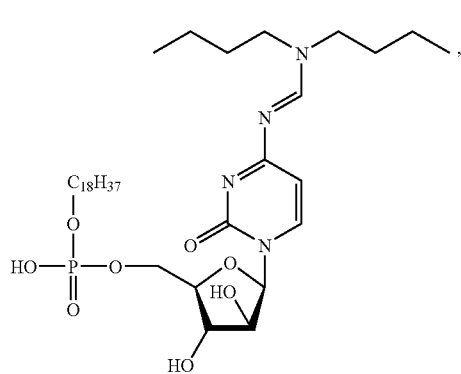
XVIII
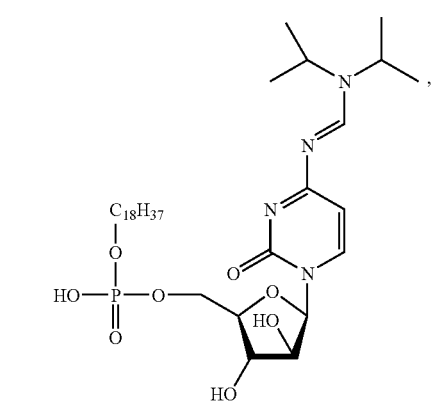
XIX
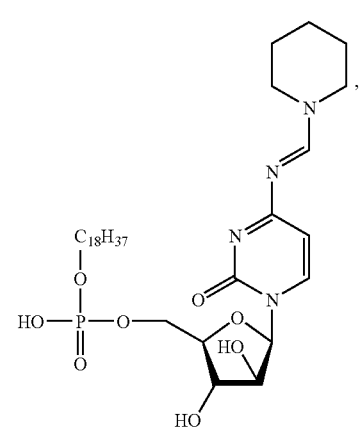
XX
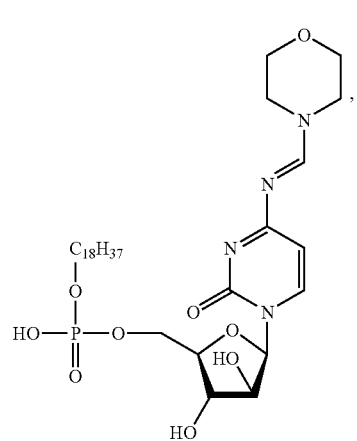
XXI
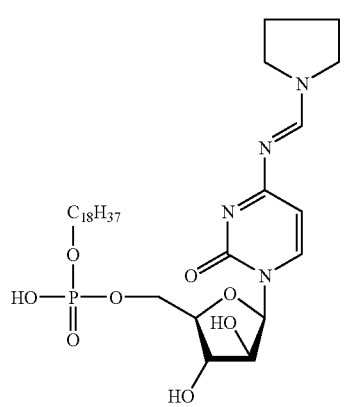
XXII and
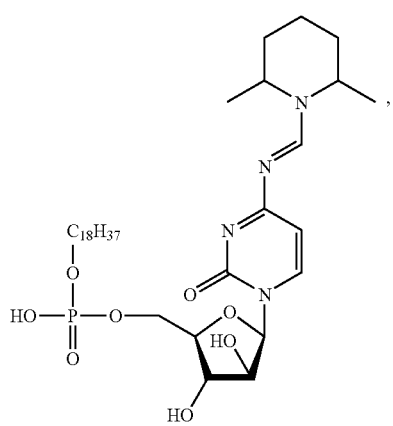
XXIII The present invention also provides a compound of formula I:

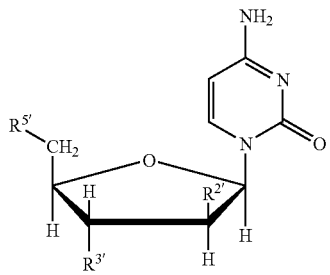

or a pharmaceutically acceptable salt thereof; wherein $R^{2'}$ and $R^{3'}$ are independently —OH or a pharmaceutically acceptable leaving group which is capable of being converted into —OH, F or —CH$_3$ when the compound represented by formula I is administered in vivo, and $R^{5'}$ is a straight or branched chain C$_9$ to C$_{24}$ alkylphosphate or a straight or branched chain C$_9$ to C$_{24}$ alkenylphosphate group or a pharmaceutically acceptable leaving group which is capable of being converted into —OH or phosphate when the compound represented by formula I is administered in vivo; in association with any other anti-viral agent as set forth in the "Pharmaceutical Compositions" section below, for example, one or more members selected from the group consisting of pegylated interferon alfa-2a, pegylated interferon alfa-2b, pegylated interferon alfa-2c, pegylated interferon alfa n-1, pegylated interferon alfa n-3, pegylated consensus interferon, interferon alfa-2a, interferon alfa-2b, interferon alfa-2c, interferon alfa n-1, interferon alfa n-3 and consensus interferon. In an embodiment, the compound represented by structural formula I is represented by the following structural formula:

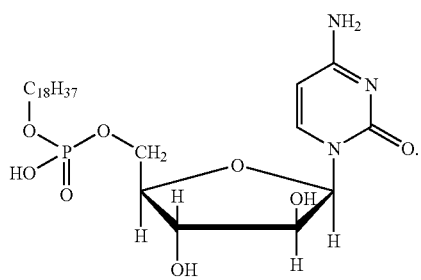

DETAILED DESCRIPTION OF THE INVENTION

The present invention provides compositions and methods or treating or preventing an infection by a virus which is a member of the Flaviviridae family in a host. For example, the present invention includes, but is not limited to methods for treating or preventing infections caused by members of the Hepacivirus genus which includes the hepatitis C virus (HCV). HCV includes several types, subtypes and isolates:

hepatitis C virus (isolate 1)
hepatitis C virus (isolate BK)
hepatitis C virus (isolate EC1)
hepatitis C virus (isolate EC10)
hepatitis C virus (isolate HC-J2)
hepatitis C virus (isolate HC-J5)
hepatitis C virus (isolate HC-J6)
hepatitis C virus (isolate HC-J7)
hepatitis C virus (isolate HC-J8)
hepatitis C virus (isolate HC-JT)
hepatitis C virus (isolate HCT18)
hepatitis C virus (isolate HCT27)
hepatitis C virus (isolate HCV-476)
hepatitis C virus (isolate HCV-KF)
hepatitis C virus (isolate Hunan)
hepatitis C virus (isolate Japanese)
hepatitis C virus (isolate Taiwan)
hepatitis C virus (isolate TH)
hepatitis C virus isolate H
hepatitis C virus type 1
hepatitis C virus type 1a
    hepatitis C virus strain H77
hepatitis C virus type 1b
hepatitis C virus type 1c
hepatitis C virus type 1d
hepatitis C virus type 1e
hepatitis C virus type 1f
hepatitis C virus type 10
hepatitis C virus type 2
hepatitis C virus type 2a
hepatitis C virus type 2b
hepatitis C virus type 2c
hepatitis C virus type 2d
hepatitis C virus type 2f
hepatitis C virus type 3
hepatitis C virus type 3a
hepatitis C virus type 3b
hepatitis C virus type 3g
hepatitis C virus type 4
hepatitis C virus type 4a
hepatitis C virus type 4c
hepatitis C virus type 4d
hepatitis C virus type 4f
hepatitis C virus type 4h
hepatitis C virus type 4k
hepatitis C virus type 5
hepatitis C virus type 5a
hepatitis C virus type 6
hepatitis C virus type 6a
hepatitis C virus type 7
hepatitis C virus type 7a
hepatitis C virus type 7b
hepatitis C virus type 8
hepatitis C virus type 8a The present invention also includes methods for treating or preventing infection caused by members of the Flavivirus genus. The Flavivirus genus includes Yellow fever virus; Tick-borne viruses such as the Gadgets Gully virus, Kadam virus, Kyasanur Forest disease virus, Langat virus, Omsk hemorrhagic fever virus, Powassan virus, Royal Farm virus, Karshi virus, Tick-borne encephalitis virus, Neudoerfl virus, Sofjin virus, Louping ill virus and the Negishi virus; seabird tick-borne viruses such as the Meaban virus, Saumarez Reef virus, and the Tyuleniy virus; mosquito-borne viruses such as the Aroa virus, Bussuquara virus, Iguape virus and the Naranjal virus; Dengue viruses such as the Dengue virus and the Kedougou virus; Japanese encephalitis viruses such as the Cacipacore virus, Koutango virus, Japanese encephalitis virus, Murray Valley encephalitis virus, Alfuy virus, St. Louis encephalitis virus, Usutu virus, West Nile virus, Kunjin virus and the Yaounde virus; Kokobera viruses such as the Kokobera virus and the Stratford virus; Ntaya viruses such as the Bagaza virus, Ilheus virus, Rocio virus, Israel turkey meningoencephalomyelitis virus, Ntaya virus and the Tembusu virus; Spondweni viruses such as the Zika virus and the Spondweni virus; Yellow fever viruses such as the Banzi virus, Bouboui virus, Edge Hill virus, Jugra virus, Saboya virus, Potiskum virus, Sepik virus, Uganda S virus, Wesselsbron virus and the Yellow fever virus; Entebbe viruses such as the Entebbe bat virus, Sokoluk virus, and the Yokose virus; Modoc viruses such as the Apoi virus, Cowbone Ridge virus, Jutiapa virus, Modoc virus, Sal Vieja virus and the San Perlita virus; Rio Bravo viruses such as the Bukalasa bat virus, Carey Island virus, Dakar bat virus, Montana myotis leukoencephalitis virus, Phnom Penh bat virus, Batu Cave virus, Rio Bravo virus, Tamana bat virus, and the Cell fusing agent virus.

The present invention includes methods for treating or preventing infection caused by members of the *Pestivirus* genus. The *Pestivirus* genus includes, Border disease virus (sheep), Bovine viral diarrhea virus 1, Bovine viral diarrhea virus 2, Classical swine fever virus, and Hog cholera virus.

Moreover, the present invention includes methods for treating or preventing infections caused by Hepatitis G virus or Hepatitis GB virus-A, B or C.

A "host", "subject" or "patient" may be any organism, such as a mammal (e.g., primate, dog, cat, cow, horse, pig, goat, rat, mouse, bird), preferably a human.

A person suffering from chronic hepatitis C infection may exhibit one or more of the following signs or symptoms:
(a) elevated ALT,
(b) positive test for anti-HCV antibodies,
(c) presence of HCV as demonstrated by a positive test for HCV-RNA,
(d) clinical stigmata of chronic liver disease,
(e) hepatocelluar damage.

A patient or host suffering from an infection by a Flaviviridae virus, such as HCV (e.g., a chronic or acute HCV infection), can be treated by administering to the patient a compound represented by structural formula I:

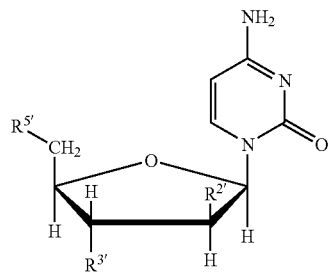

or a pharmaceutically acceptable salt thereof.

$R^{2'}$ and $R^{3'}$ are independently —OH or a pharmaceutically acceptable leaving group which is capable of being converted to phosphate, —OH, —F or —CH$_3$ when the compound represented by formula I is administered in vivo.

$R^{5'}$ is a straight or branched chain $C_9$ to $C_{24}$ alkylphosphate (e.g., $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$ or $C_{24}$ alkylphosphate, including $C_{16}$ to $C_{20}$ alkylphosphate or $C_{18}$ to $C_{20}$ alkylphosphate) or straight or branched chain $C_9$ to $C_{24}$ alkenylphosphate (e.g., $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$ or $C_{24}$ alkenylphosphate, including $C_{18}$ to $C_{20}$ alkenylphosphate) group or a pharmaceutically acceptable leaving group which is capable of being converted to —OH or phosphate when the compound represented by formula I is administered in vivo.

For example, the compound can be represented by structural formula II:

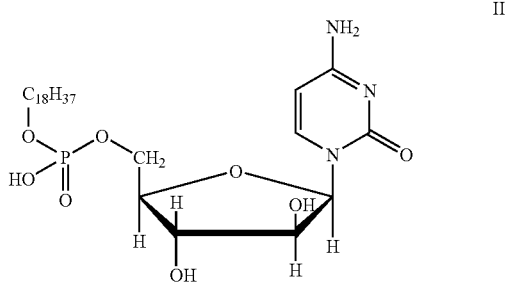

The compound represented by structural formula II is also known as Fosteabine and as YNK01. Fosteabine is an orally active derivative of cytarabine which is sold by Nippon Kayaku Co. Ltd. (Tokyo, Japan).

Furthermore, a patient suffering from an infection by a flaviviridae virus, such as HCV (e.g., a chronic HCV infection), can be treated by administering to the patient a compound represented by structural formula IV:

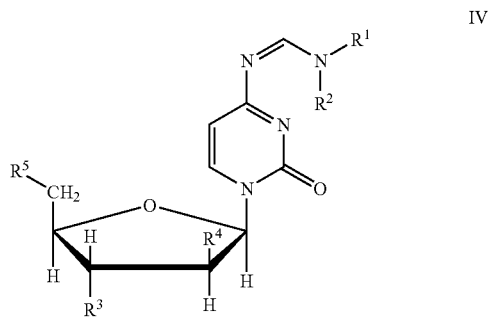

or a pharmaceutically acceptable salt thereof.

$R^3$ and $R^4$ are independently —OH or a pharmaceutically acceptable leaving group which is capable of being converted to —F, —CH$_3$—OH or phosphate when the compound represented by formula IV is administered in vivo, wherein $R^5$ is —OH, a straight or branched chain $C_9$ to $C_{24}$ alkylphosphate (e.g., —OPO$_3$—C$_{18}$H$_{37}$ or as described above) or a straight or branched chain $C_9$ to $C_{24}$ alkenylphosphate group (e.g., as described above) or a pharmaceutically acceptable leaving group which is capable of being converted into —OH, phosphate, F or —CH$_3$ when the compound represented by formula IV is administered in vivo and wherein $R^1$ and $R^2$ are independently $C_1$ to $C_{10}$ alkyl or $R^1$ and $R^2$ taken together with the N form a $C_3$ to $C_7$ ring represented by the following structural formula:

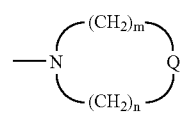

wherein n and m are independently 0, 1, 2 or 3 and Q is CH$_2$, NR, S, SO or SO$_2$ and R is independently H, $C_1$ to $C_6$ alkyl or acyl. Such compounds are discussed for example, in Kerr et al., J. Pharm Sci. 83(4):582-586 (1994).

In an embodiment of the invention, a compound represented by structural formula VI, VII, VIII, IX, X, XI, XII, XIII, XIV, XV, XVI, XVI, XVII, XVIII, XIX, XX, XXI, XXII or XXIII:
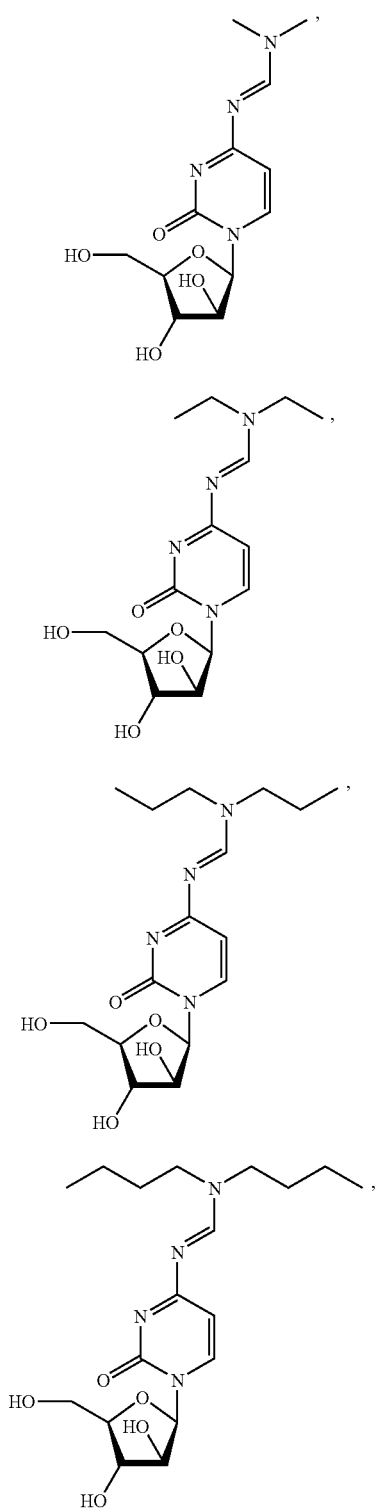
VI
VII
VIII
IX
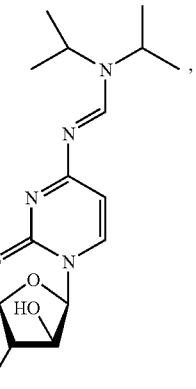
X
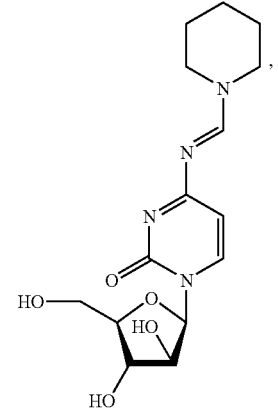
XI
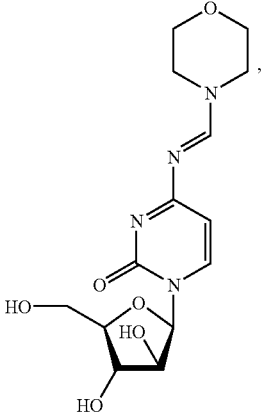
XII
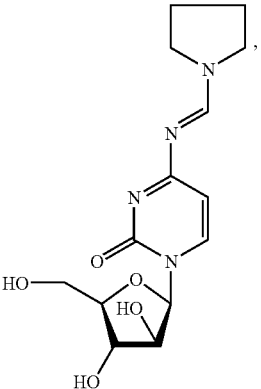
XIII

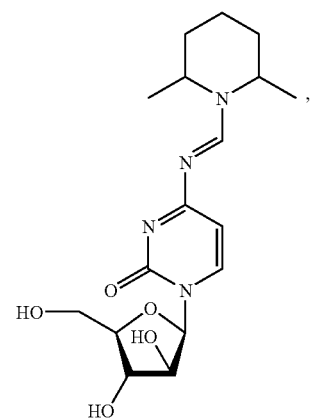XIV
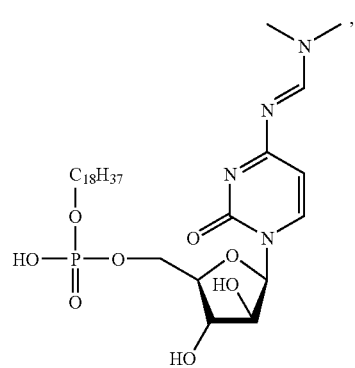XV
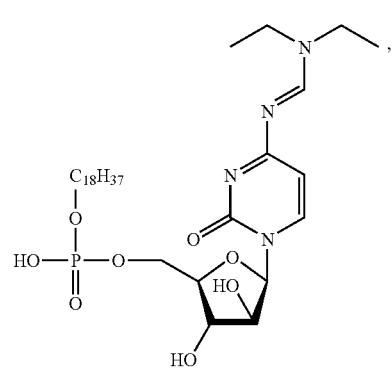XVI
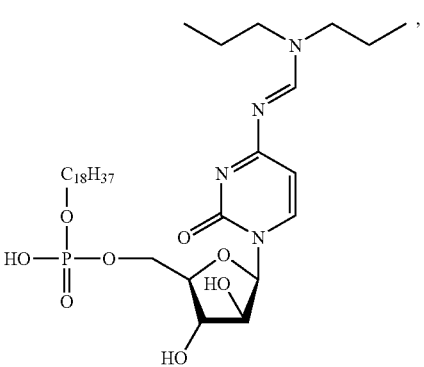XVII
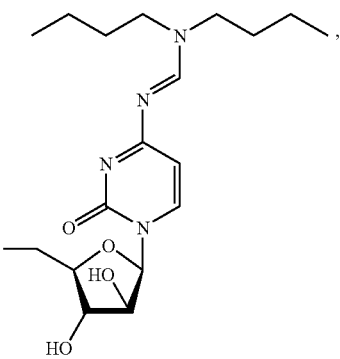XVIII
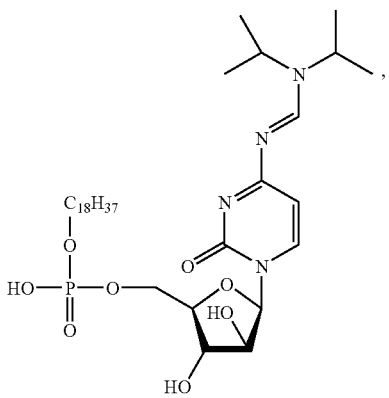XIX
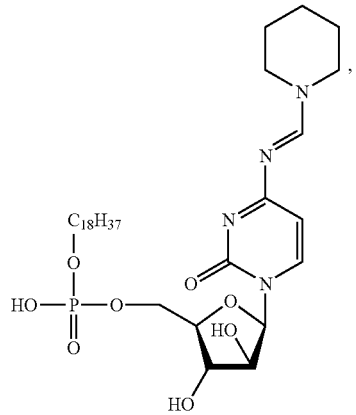XX
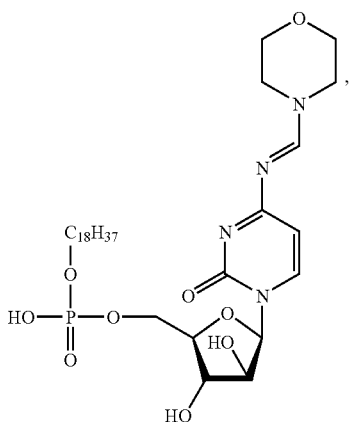XXI

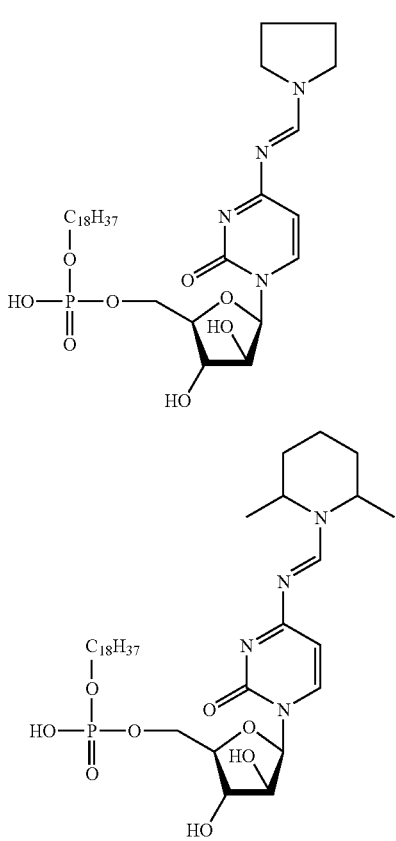

can be administered to a host suffering from a Flaviviridae (e.g., HCV) infection (e.g., chronic HCV infection).

A compound represented by a structural formula selected from I-XXIII can also be administered to a patient in association with one or more other anti-viral agents such as pegylated or unpegylated interferon alfa-2a, pegylated or unpegylated interferon alfa-2b, pegylated or unpegylated interferon alfa-2c, pegylated or unpegylated interferon alfa n-i, pegylated or unpegylated interferon alfa n-3 or pegylated or unpegylated consensus interferon.

"Phosphate" refers to —O—PO$_3$H$_2$ or any of its corresponding ions.

The term "alkyl" as used herein means straight and branched carbon chains of one to twenty four carbons (e.g., $C_1$, $C_2$, $C_3$, $C_4$, $C_5$, $C_6$, $C_7$, $C_8$, C9, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$ or $C_{24}$).

"Alkylphosphate" is —O—PO$_3$H-alkyl or any of its corresponding ions.

The term "alkenyl" or "alkene" as used herein means straight and branched chain alkyl groups containing at least one carbon-carbon double bond and two to twenty four carbons (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$ or $C_{24}$).

"Alkenylphosphate" is —O—PO$_3$H-alkene or any of its corresponding ions.

The term "aryl" represents a carbocyclic group (e.g., monocyclic or multicyclic) containing from 6 to 15 carbon atoms and having at least one aromatic ring (e.g., phenyl ring or naphthyl ring).

As used herein, the term "heteroaryl" refers to an aryl group having one or more heteroatoms in the aromatic rings (e.g., N, O or S).

The term "arylalkyl" or "aralkyl" as used herein means an alkyl group substituted by an aryl group.

The term "cycloalkyl" as used herein means carbocyclic rings of three to twelve carbons, preferably three to seven carbons and more preferably three to six carbons optionally substituted by one or more double bonds.

"Acyl" means a radical of a carboxylic acid having the formula. alkyl-C(O)—, aryl-C(O)—, aralkyl-C(O)—, ($C_3$-$C_7$)cycloalkyl-C(O)—, ($C_3$-$C_7$)cycloalkyl-($C_1$-$C_6$)alkyl-C(O)—, and heteroaryl-C(O)—, wherein alkyl, aralkyl and heteroaryl are as defined herein; aryl is phenyl or naphthyl; and aralkyl is aryl-($C_1$-$C_6$)alkyl, wherein aryl is as defined above.

Methyl is —CH$_3$. Ethyl is —CH$_2$—CH$_3$. n-propyl is —CH$_2$CH$_2$CH$_3$. i-propyl is —CH—(CH$_3$)$_2$. n-butyl is —CH$_2$CH$_2$CH$_2$CH$_3$.

The term "pharmaceutically acceptable leaving group" refers to a leaving group which, when administered to a host in accordance with the invention, is non-toxic and includes amino acids residues, carbohydrate residues, peptide residues and cholesterol residues ( (

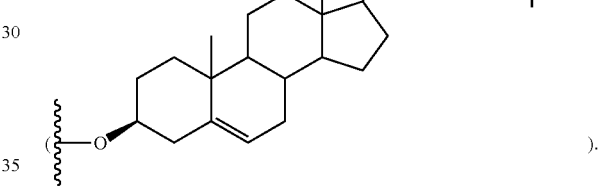

).

For example, an amino acid pharmaceutically acceptable leaving group can be a natural or unnatural α-amino acid residue:

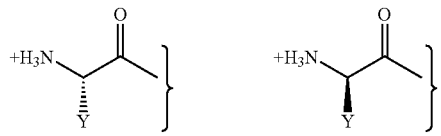

wherein Y=H, CH$_3$; CH$_3$CH$_2$—; CH$_3$CH$_2$CH$_2$—; Me$_2$CH—; Me$_2$CH$_2$CH$_2$—; CH$_3$CH$_2$CH(Me)-PhCH$_2$—; HOOCCH$_2$CH$_2$—; HSCH$_2$—; HOOCCH$_2$—; MeSCH$_2$CH$_2$—; HOCH$_2$—;

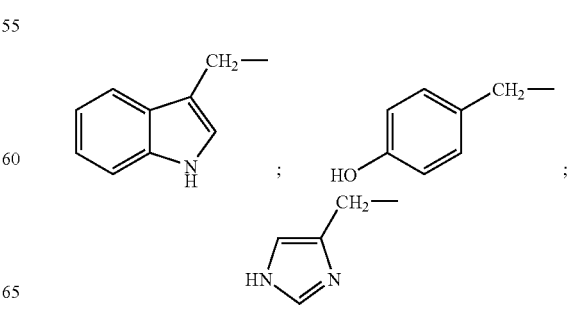

or Y is H₂N(CH₂)₄— or CH₃CH(OH)—; or a pharmaceutically acceptable salt thereof;

or Y taken together with the α carbon and N form

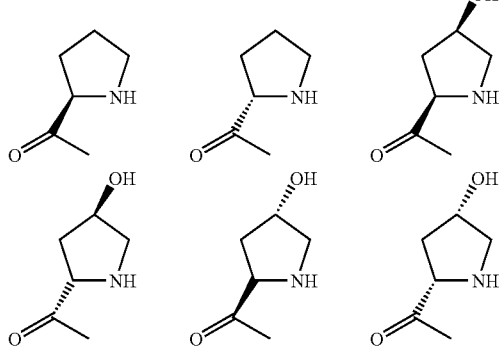

or a pharmaceutically acceptable salt thereof. A pharmaceutically acceptable peptide residue leaving group can be, for example, a combination of two or more of the amino acids set forth above (e.g., dipeptide or tripeptide). Furthermore, a pharmaceutically acceptable carbohydrate residue leaving group can be, for example, a monosaccharide such as glucose

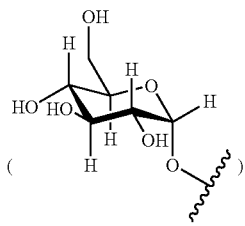

or galactose

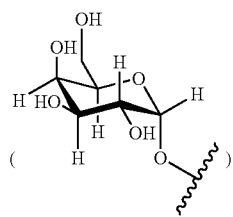

or a combination of two or more monosaccharides such as lactose

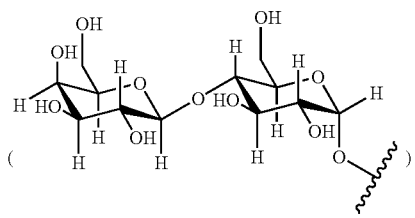

or sucrose

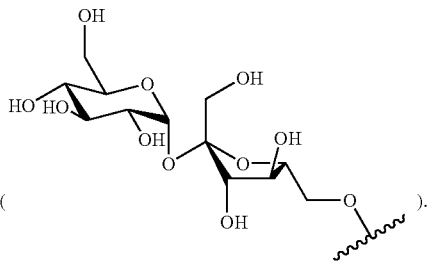

Synthesis of the compounds of the invention, comprising such leaving groups can be done by any practitioner of ordinary skill in the art (see, for example, *Protective Groups in Organic Synthesis*, by Theodora W. Greene, Peter G. M. Wuts; John Wiley & Sons, Inc. New York (1991)).

In a liver transplantation procedure, the donor liver can come from a living donor (i.e., living donor liver transplantation (LDLT)) wherein a portion of the donor's liver is removed and introduced into the recipient. Alternatively, the transplant can be from a deceased donor wherein the entire liver is removed and transplanted.

The scope of the present invention also includes compounds represented by structural formula IV:

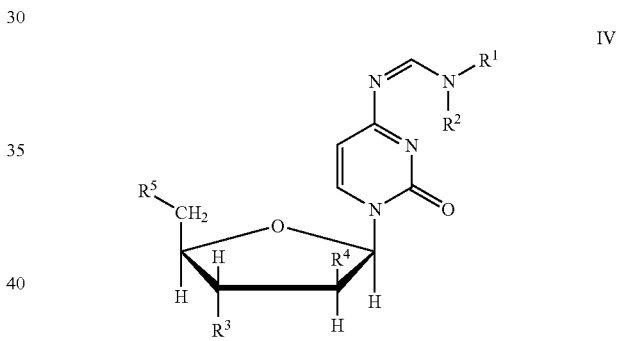

IV or a pharmaceutically acceptable salt thereof; wherein $R^3$ and $R^4$ are independently —OH or a pharmaceutically acceptable leaving group which is capable of being converted to phosphate, —OH, F or —CH₃ when the compound represented by formula IV is administered in vivo, wherein $R^5$ is a straight or branched chain $C_9$ to $C_{24}$ alkylphosphate (e.g., —OPO₃— $C_{18}H_{37}$) or a straight or branched chain $C_9$ to $C_{24}$ alkenylphosphate group and wherein $R^1$ and $R^2$ are independently $C_1$ to $C_{10}$ alkyl or wherein $R^1$ and $R^2$ taken together with N form a $C_3$ to $C_7$ ring represented by the following structural formula:

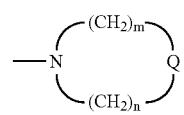

wherein n and m are independently 0, 1, 2 or 3 and Q is CH₂, NR, O, S, SO or SO₂; and R is independently H, $C_1$ to $C_6$ alkyl or $C_1$ to $C_6$ acyl or wherein $R^1$ and $R^2$, taken together with the N, are represented by the structural formula:

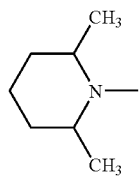

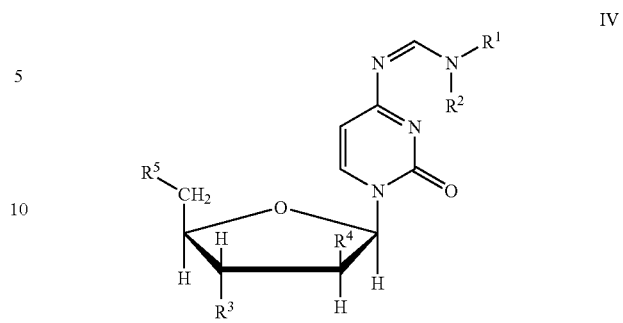

along with pharmaceutical compositions thereof which further comprise a pharmaceutically acceptable carrier. Also within the scope of the present invention is any compound represented by a structural formula selected from the group consisting of XV-XXIII along with pharmaceutically acceptable salts thereof and pharmaceutical compositions thereof further comprising a pharmaceutically acceptable carrier.

The scope of the present invention also includes compositions comprising a compound represented by structural formula I:

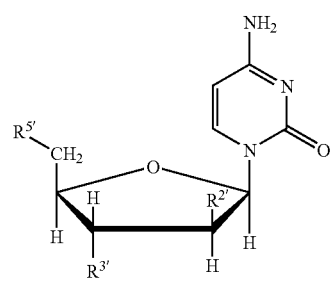

or a pharmaceutically acceptable salt thereof; wherein $R^{2'}$ and $R^{3'}$ are independently —OH or a pharmaceutically acceptable leaving group which is capable of being converted into phosphate, —OH, F or —$CH_3$ when the compound represented by formula I is administered in vivo, and $R^{5'}$ is a straight or branched chain $C_9$ to $C_{24}$ alkylphosphate or a straight or branched chain $C_9$ to $C_{24}$ alkenylphosphate group or a pharmaceutically acceptable leaving group which is capable of being converted into —OH or phosphate when the compound represented by formula I is administered in vivo; ) in association with one or more other anti-viral substances (e.g., a kit), for example, any other anti-viral agent disclosed under the "Pharmaceutical Compositions" section below, including, but by no means limited to, ribavirin, PEG-interferon alfa-2a, PEG-interferon alfa-2b, interferon alfa-2a or interferon alfa-2b or any other anti-viral substance described infra; along with pharmaceutical compositions thereof further comprising a pharmaceutically acceptable carrier or a compound represented by structural formula IV:

or a pharmaceutically acceptable salt thereof; wherein $R^3$ and $R^4$ are independently —OH or a pharmaceutically acceptable leaving group which is capable of being converted to phosphate, —OH, F or —$CH_3$ when the compound represented by formula IV is administered in vivo, wherein $R^5$ is —OH, a straight or branched chain $C_9$ to $C_{24}$ alkylphosphate (e.g., —$OPO_3$—$C_{18}H_{37}$) or a straight or branched chain $C_9$ to $C_{24}$ alkenylphosphate group or a pharmaceutically acceptable leaving group which is capable of being converted into —OH, phosphate, F or —$CH_3$ when the compound represented by formula IV is administered in vivo; and wherein $R^1$ and $R^2$ are independently $C_1$ to $C_{10}$ alkyl or wherein $R^1$ and $R^2$ taken together with N form a $C_3$ to $C_7$ ring represented by the following structural formula:

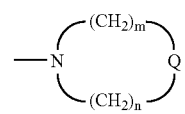

wherein n and m are independently 0, 1, 2 or 3 and Q is $CH_2$, NR, O, S, SO or $SO_2$; and R is independently H, $C_1$ to $C_6$ alkyl or $C_1$ to $C_6$ acyl or wherein $R^1$ and $R^2$, taken together with the N, are represented by the structural formula:

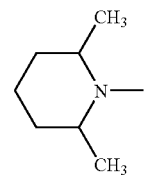

(e.g., any compound represented by a structural formula selected from VI-XXIII) optionally in association with one or more further anti-viral substances (e.g., a kit) for example, any other anti-viral agent disclosed under the "Pharmaceutical Compositions" section below including, but by no means limited to, ribavirin, PEG-interferon alfa-2a, PEG-interferon alfa-2b, interferon alfa-2a or interferon alfa-2b or any other anti-viral substance described infra; along with pharmaceutical compositions thereof further comprising a pharmaceutically acceptable carrier.

Pharmaceutical Compositions

The present invention includes methods for using a pharmaceutical composition comprising a compound of the present invention (e.g., compound represented by a formula selected from I-XXIII) and a pharmaceutically acceptable carrier for treating a Flaviviridae infection. The pharmaceutical compositions may be prepared by any methods well known in the art of pharmacy; see, e.g., Gilman, et al., (eds.) (1990), *The Pharmacological Bases of Therapeutics,* 8th Ed., Pergamon Press; A. Gennaro (ed.), *Remington's Pharmaceutical Sciences,* 18th Edition, (1990), Mack Publishing Co., Easton, Pa.; Avis, et al., (eds.) (1993) *Pharmaceutical Dosage Forms: Parenteral Medications Dekker,* New York; Lieberman, et al., (eds.) (1990) *Pharmaceutical Dosage Forms: Tablets* Dekker, New York; and Lieberman, et al., (eds.) (1990), *Pharmaceutical Dosage Forms: Disperse Systems* Dekker, New York.

A pharmaceutical composition containing a compound of the present invention (e.g., represented by a formula selected from I-XXIII) can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like. All routes of administration are contemplated including, but not limited to, parenteral (e.g., subcutaneous, intravenous, intraperitoneal, intramuscular) and non-parenteral (e.g., oral, transdermal, intranasal, intraocular, sublingual, inhalation, rectal and topical).

Unit forms of administration include oral forms such as tablets, capsules, powders, cachets, granules and solutions or suspensions, sublingual and buccal forms of administration, aerosols, implants, subcutaneous, intramuscular, intravenous, intranasal, intraocular, subcutaneous or rectal forms of administration.

When a solid composition is prepared in the form of tablets, e.g., a wetting agent such as sodium lauryl sulfate can be added to micronized or non-micronized compounds and mixed with a pharmaceutical vehicle such as silica, gelatin starch, lactose, magnesium stearate, talc, gum arabic or the like. The tablets can be coated with sucrose, various polymers, or other appropriate substances. Tablets can be treated so as to have a prolonged or delayed activity and so as to release a predetermined amount of active principle continuously or at predetermined intervals, e.g., by using ionic resins and the like.

A preparation in the form of gelatin capsules may be obtained, e.g., by mixing a compound of the present invention (e.g., represented by a formula selected from I-XXIII) with a diluent, such as a glycol or a glycerol ester, and incorporating the resulting mixture into soft or hard gelatin capsules.

A preparation in the form of a syrup or elixir can contain a compound of the present invention (e.g., represented by a formula selected from I-XXIII), e.g., with a sweetener, methylparaben and propylparaben as antiseptics, flavoring agents and an appropriate color.

Water-dispersible powders or granules can contain a compound of the present invention (e.g., represented by a formula selected from I-XXIII) mixed, e.g., with dispersants, wetting agents or suspending agents, such as polyvinylpyrrolidone, as well as with sweeteners and/or other flavoring agents.

Rectal administration may be provided by using suppositories which may be prepared, e.g., with binders melting at the rectal temperature, for example cocoa butter or polyethylene glycols.

Parenteral, intranasal or intraocular administration may be provided by using, e.g., aqueous suspensions, isotonic saline solutions or sterile and injectable solutions containing pharmacologically compatible dispersants and/or solubilizers, for example, propylene glycol or polyethylene glycol.

Thus, to prepare an aqueous solution for intravenous injection, it is possible to use a co-solvent, e.g., an alcohol such as ethanol or a glycol such as polyethylene glycol or propylene glycol, and a hydrophilic surfactant such as Tween® 80. An oily solution injectable intramuscularly can be prepared, e.g., by solubilizing the active principle with a triglyceride or a glycerol ester.

Topical administration can be provided by using, e.g., creams, ointments or gels.

Transdermal administration can be provided by using patches in the form of a multilaminate, or with a reservoir, containing an a compound of the invention (e.g., represented by a formula selected from I-XXIII) and an appropriate solvent.

Administration by inhalation can be provided by using, e.g., an aerosol containing sorbitan trioleate or oleic acid, for example, together with trichlorofluoromethane, dichlorofluoromethane, dichlorotetrafluoroethane or any other biologically compatible propellant gas; it is also possible to use a system containing a compound of the present invention (e.g., represented by a formula selected from I-XXIII), by itself or associated with an excipient, in powder form.

A compound of the present invention (e.g., represented by a formula selected from I-XXIII) can also be formulated as microcapsules or microspheres, e.g., liposomes, optionally with one or more carriers or additives.

Implants are among the prolonged release forms which can be used in the case of chronic treatments. They can be prepared in the form of an oily suspension or in the form of a suspension of microspheres in an isotonic medium.

Methods of the present invention can include administration of a compound of the present invention (e.g., represented by a formula selected from I-XXIII) in association with, for example, one or more other anti-viral agents. The administration and dosage of such agents is typically as according to the schedule listed in the product information sheet of the approved agents, in the *Physicians' Desk Reference* 2003 *(Physicians' Desk Reference,* 57th Ed); Medical Economics Company; ISBN: 1563634457; 57th edition (November 2002), as well as therapeutic protocols well known in the art. Furthermore, the present invention includes compositions comprising a compound represented by structural formula IV (e.g., as described herein) in association with one or more other anti-viral agents (e.g., any of those described herein); in an embodiment of the invention, the compound represented by structural formula IV is a compound represented by a structural formula selected from the group consisting of formulas VI-XXIII.

Suitable other anti-viral agents include, but are not limited to, pegylated or unpegylated interferon alfa-2a, pegylated or unpegylated interferon alfa-2b, pegylated or unpegylated interferon alfa-2c, pegylated or unpegylated interferon alfa n-1, pegylated or unpegylated interferon alfa n-3 and pegylated, unpegylated consensus interferon or albumin-interferon-alpha.

The term "interferon alpha" as used herein means the family of highly homologous species-specific proteins that inhibit viral replication and cellular proliferation and modulate immune response. Typical suitable interferon-alphas include, but are not limited to, recombinant interferon alpha-2b, recombinant interferon alpha-2a, recombinant interferon alpha-2c, alpha 2 interferon, interferon alpha-n1 (INS), a purified blend of natural alpha interferons, a consensus alpha interferon such as those described in U.S. Pat. Nos. 4,897,471 and 4,695,623 (especially Examples 7, 8 or 9 thereof), or interferon alpha-n3, a mixture of natural alpha interferons.

Interferon alfa-2a is sold as ROFERON-A® by Hoffmann-La Roche (Nutley, N.J).

Interferon alfa-2b is sold as INTRON-A® by Schering Corporation (Kenilworth, N.J.). Interferon alfa-2b is also sold, in combination with ribavirin, as REBETRON® by Schering Corporation (Kenilworth, N.J.). The manufacture of interferon alpha 2b is described, for example, in U.S. Pat. No. 4,530,901.

Interferon alfa-n3 is a mixture of natural interferons sold as ALFERON N INJECTION® by Hemispherx Biopharma, Inc. (Philadelphia, Pa.).

Interferon alfa-n1 (INS) is a mixture of natural interferons sold as WELLFERON® by Glaxo-Smith-Kline (Research Triangle Park, N.C.).

Consensus interferon is sold as INFERGEN® by Intermune, Inc. (Brisbane, Calif.).

Interferon alfa-2c is sold as BEROFOR® by Boehringer Ingelheim Pharmaceutical, Inc. (Ridgefield, Conn.).

A purified blend of natural interferons is sold as SUMIFERON® by Sumitomo; Tokyo, Japan.

Pegylated interferon alpha may also be administered in association with a compound of the invention (e.g., represented by a formula selected from I-XXIII). The term "pegylated interferon alpha" as used herein means polyethylene glycol modified conjugates of interferon alpha, preferably interferon alpha-2a and alpha-2b. The preferred polyethylene-glycol-interferon alpha-2b conjugate is PEG 12000-interferon alpha-2b. The phrases "12,000 molecular weight polyethylene glycol conjugated interferon alpha" and "PEG 12000-IFN alpha" as used herein include conjugates such as are prepared according to the methods of International Application No. WO 95/13090 and containing urethane linkages between the interferon alpha-2a or -2b amino groups and polyethylene glycol having an average molecular weight of 12000. The pegylated inteferon alpha, PEG 12000-IFN-alpha-2b is available from Schering-Plough Research Institute, Kenilworth, N.J.

The preferred PEG 12000-interferon alpha-2b can be prepared by attaching a PEG polymer to the epsilon amino group of a lysine residue in the interferon alpha-2b molecule. A single PEG 12000 molecule can be conjugated to free amino groups on an IFN alpha-2b molecule via a urethane linkage. This conjugate is characterized by the molecular weight of PEG 12000 attached. The PEG 12000-IFN alpha-2b conjugate can be formulated as a lyophilized powder for injection.

Pegylated interferon alfa-2b is sold as PEG-INTRON® by Schering Corporation (Kenilworth, N.J.).

Pegylated interferon-alfa-2a is sold as PEGASYS® by Hoffmann-La Roche (Nutley, N.J.).

Other interferon alpha conjugates can be prepared by coupling an interferon alpha to a water-soluble polymer. A non-limiting list of such polymers include other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alpha-polymer conjugates are described, for example, in U.S. Pat. No. 4,766,106, U.S. Pat. No. 4,917, 888, European Patent Application No. 0 236 987 or 0 593 868 or International Publication No. WO 95/13090.

Pharmaceutical compositions of pegylated interferon alpha suitable for parenteral administration can be formulated with a suitable buffer, e.g., Tris-HCl, acetate or phosphate such as dibasic sodium phosphate/monobasic sodium phosphate buffer, and pharmaceutically acceptable excipients (e.g., sucrose), carriers (e.g. human plasma albumin), toxicity agents (e.g., NaCl), preservatives (e.g., thimerosol, cresol or benzyl alcohol), and surfactants (e.g., tween or polysorbates) in sterile water for injection. The pegylated interferon alpha can be stored as lyophilized powders under refrigeration at 2°-8° C. The reconstituted aqueous solutions are stable when stored between 2° and 8° C. and used within 24 hours of reconstitution. See for example U.S. Pat. Nos. 4,492,537; 5,762,923 and 5,766,582. The reconstituted aqueous solutions may also be stored in prefilled, multi-dose syringes such as those useful for delivery of drugs such as insulin. Typical, suitable syringes include systems comprising a prefilled vial attached to a pen-type syringe such as the NOVOLET® Novo Pen available from Novo Nordisk or the REDIPEN®, available from Schering Corporation, Kenilworth, N.J. Other syringe systems include a pen-type syringe comprising a glass cartridge containing a diluent and lyophilized pegylated interferon alpha powder in a separate compartment.

In an embodiment of the invention, one or more other anti-viral substances may be administered with one or more compounds of the invention (e.g., represented by a structural formula selected from I-XXIII). For example, a compound of the invention (e.g., represented by a formula selected from I-XXIII) may be administered with interferon-alfa, pegylated interferon-alfa or albumin-interferon.

Other types of compounds which may be administered with a compound of the invention (e.g., represented by a structural formula selected from I-XXIII) include ribonucleoside analogues, IMPDH inhibitors, N-glycosylation inhibitors, N3 protease inhibitors, NS5B inhibitors, immunomodulatory compounds and CTP synthase inhibitors, thiazolidine derivatives, benzanilides, phenanthrenequinones, helicase inhibitors, polymerase inhibitors, antisense phosphothioate oligodeoxynucleotides, IRES-dependent translation inhibitors, nuclease resistant ribozymes, 1-amino-alkyloyclohexanes, alkyl lipids, antioxidants, squalene, amantadine, bile acids, N-(phosphonoacetyl)-L-aspartic acid, benzenedicarboxamides, polyadenylic acid derivatives, 2',3' dideoxyinosine and benzimidazoles.

In an embodiment of the present invention, ribavirin

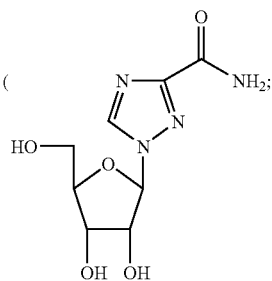

1-β-D-ribofuranosyl-1H-1 ,2,4-triazole-3-carboxamide) is administered in association with a compound of the present invention (e.g., represented by a formula selected from I-XXIII). Ribavirin is sold as REBETOL® by Schering Corporation; Kenilworth, N.J. Its manufacture and formulation is described, for example, in U.S. Pat. No. 4,211,771. A combination of ribavirin and recombinant interferon alfa-2b (REBETRON®; Schering Corporation; Kenilworth, N.J.) may also be administered in association with a compound of the invention (e.g., represented by a formula selected from I-XXIII).

In another embodiment of the invention, gemcitabine (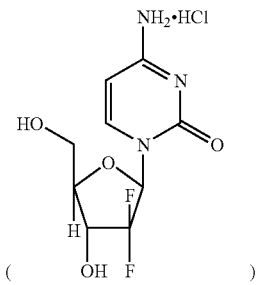)

is administered in association with a compound of the present invention (e.g., represented by a formula selected from I-XXIII). Gemcitabine is sold as GEMZAR® by Eli Lilly and Co. (Indianapolis, Ind.).

A further embodiment of the present invention comprises administering a compound of the invention (e.g., represented by a formula selected from I-XXIII) in association with VX497

(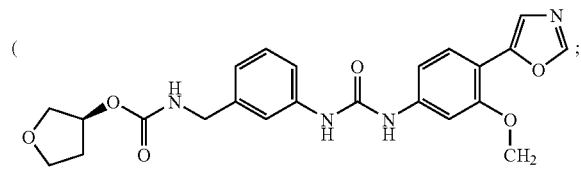)

Vertex Pharmaceuticals; Cambridge, Mass.).

An embodiment of the invention comprises administering mycophenolate mofetil (MMF; 2-morpholinoethyl (E)-6-(1, 3-dihydro-4-hydroxy-6-methoxy-7-methyl-3-oxo-5-isobenzofuranyl)-4-methyl-4-hexenoate) in association with a compound of the invention (e.g., represented by a formula selected from I-XXIII). MMF is sold as CellCept® by Roche Laboratories; Nutley, N.J.

Another embodiment comprises administering EICAR (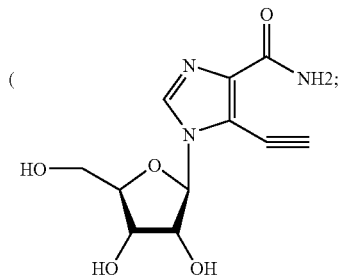)

5-ethynyl-1-beta-D-ribofuranosylimidazole-4-carboxamide; Balzarini et al., J. Biol. Chem. 268(33): 24591-24598 (1993)) in association with a compound of the invention (e.g., represented by a formula selected from I-XXIII).

An embodiment of the present invention comprises administering tiazofurin (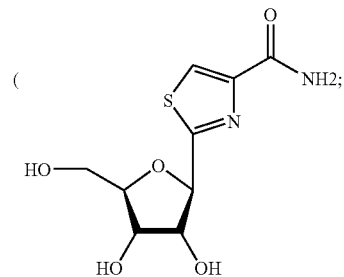)

Balzarini et al., J. Biol. Chem. 268(33): 24591-24598 (1993)) in association with a compound of the invention (e.g., represented by a formula selected from I-XXIII).

Another embodiment of the invention comprises administering deoxynojirimycin and/or derivatives thereof, such as N-nonyl-deoxynojirimycin (De Clercq et al., Mini Rev Med Chem. 2(2):163-75 (2002)) or n-butyl deoxynojirimycin (nB-DNJ; Ouzounov et al., Antiviral Res. 55(3):425-35 (2002)), in association with a compound of the invention (e.g., represented by a formula selected from I-XXIII).

In one embodiment, a compound of the present invention (e.g., represented by a formula selected from I-XXIII) is administered in association with albumin-interferon alpha (ALBUFERON™). Albumin-interferon alpha is interferon-a fused to human serum albumin. ALBUFERON™ is available from Human Genome Sciences, Rockville, Md. ALBUFERON™ has been shown to be effective for treatment of hepatitis C virus infections (Blaire et al., J. Pharm and Exp. Therap. 303(2): 540-548 (2002)).

In another embodiment, BILN-2061

(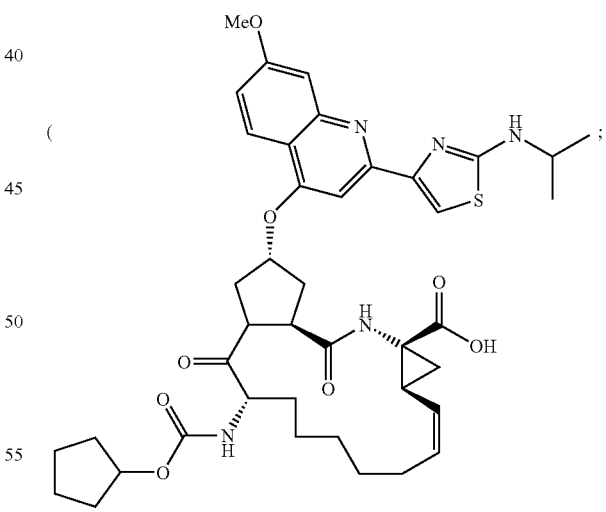)

Lamarre et al., Nature 426(6963):129-31 (2003)), is administered in association with a compound of the present invention (e.g., represented by a formula selected from I-XXIII).

In another embodiment, thymalfasin (e.g., ZADAXIN™) is administered in association with a compound of the invention (e.g., represented by a formula selected from I-XXIII). ZADAXIN™ is available from SciClone Pharmaceuticals International, Ltd., San Mateo, Calif.

In yet another embodiment, isatoribine

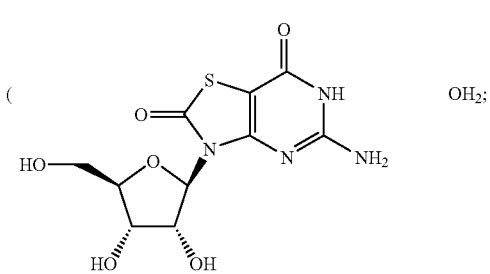

ANA245; 5-Amino-3-beta-D-ribofuranosylthiazolo(4,5-d)pyrimidine-2,7(3H,6H)-dione monohydrate; Thiazolo(4,5-d)pyrimidine-2,7(3H,4H)-dione, 5-amino-3-beta-D-ribofuranosyl-, monohydrate) is administered in association with a compound of the invention (e.g., represented by a formula selected from I-XXIII).

In another embodiment, a compound of the invention (e.g., represented by a formula selected from I-XXIII) is administered in association with an NS5B inhibitor such as NM283 or NM107 (Idenix Pharmaceuticals; Cambridge, Mass.).

In another embodiment, a compound of the invention (e.g., represented by a formula selected from I-XXIII) is administered in association with SCH68631

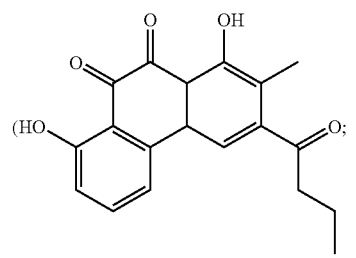

Chu et al., Tetrahedron Letters 37(40): 7229-7232 (1996)) or SCH351633

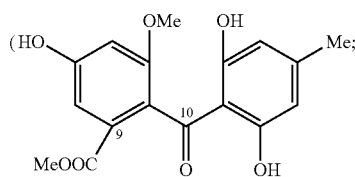

Biorg. Med. Chem. Lett. 9(14): 1949-1952 (1999)).

In a further embodiment, a compound of the invention (e.g., represented by a formula selected from I-XXIII) is administered in association with any of the $P_1$ variants of Elgin c disclosed in Qasim et al., Biochemistry 36: 1598-1607 (1997).

In yet another embodiment, a compound of the invention (e.g., represented by a formula selected from I-XXIII) is administered in association with gliotoxin

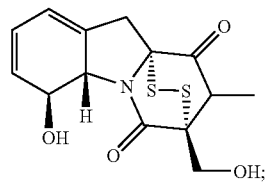

Ferrari et al., J. Virology 73(2): 1649-1654 (1999)).

Other embodiments of the invention include administering a compound of the present invention (e.g., represented by a formula selected from I-XXIII) in association with RD3-4082

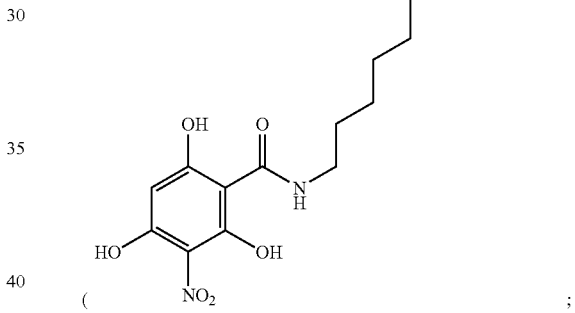

Sudo et al., Anti-viral Chem. & Chemother. 9: 186 (1998)) or with RD3-4078

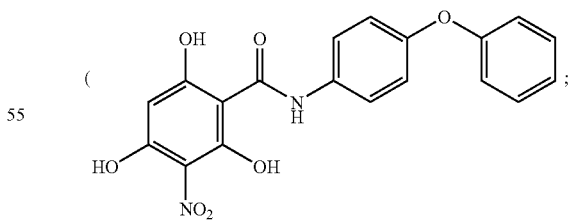

Sudo et al., Anti-viral Chem. & Chemother. 9: 186 (1998)) or any other protease inhibitor disclosed in Sudo et al.

A further embodiment of the invention comprises administering a compound of the present invention (e.g., represented by a structural formula selected from I-XXIII) in association with

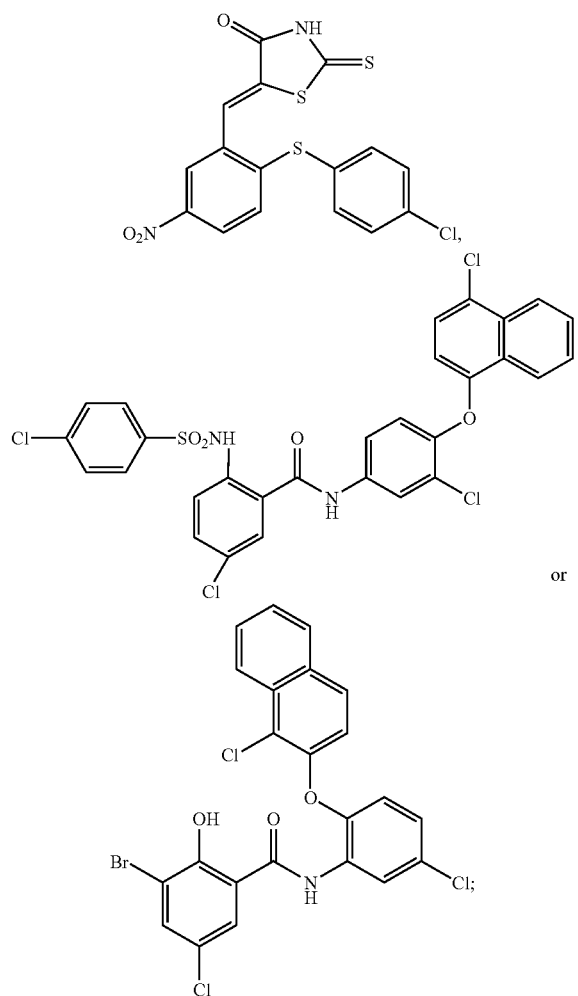

Kakiuchi et al., FEBS Letters 421: 217-220 (1998)) or any other proteinase inhibitor disclosed in Kakiuchi et al.

Another embodiment of the present invention comprises administering a compound of the present invention (e.g., represented by a structural formula selected from I-XXIII) in association with RD4-6205

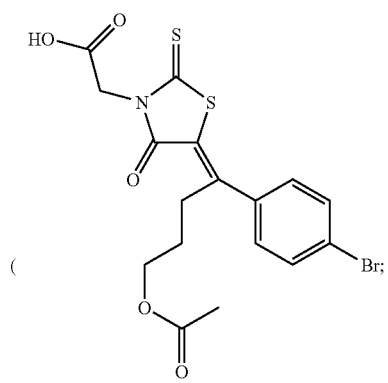

Sudo et al., Biochem. Biophys. Res. Comm. 238: 643-647 (1997)) or any other protease inhibitor disclosed in Sudo et al.

An embodiment of the present invention comprises administering a compound of the present invention (e.g., represented by a structural formula selected from I-XXIII) in association with cerulenin

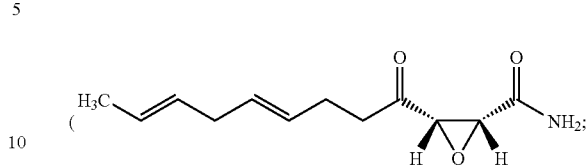

CAS Registry No. 17397-89-6; Lohmann et al., Virology 249: 108-118 (1998)) or any other HCV RNA-dependent RNA polymerase (RdRp) inhibitor disclosed in Lohmann et al.

An embodiment of the present invention comprises administering a compound of the present invention (e.g., represented by a structural formula selected from I-XXIII) in association with ceplene

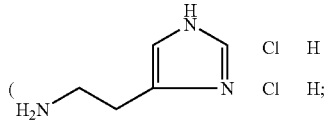

2-(1H-Imidazol-4-yl)ethanamine dihydrochloride).

Yet another embodiment of the present invention comprises administering a compound of the present invention (e.g., represented by a structural formula selected from I-XXIII) in association with amantadine

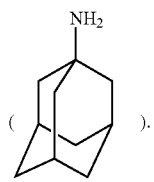

A further embodiment of the present invention comprises administering a compound of the present invention (e.g., represented by a structural formula selected from I-XXIII) in association with IDN-6556

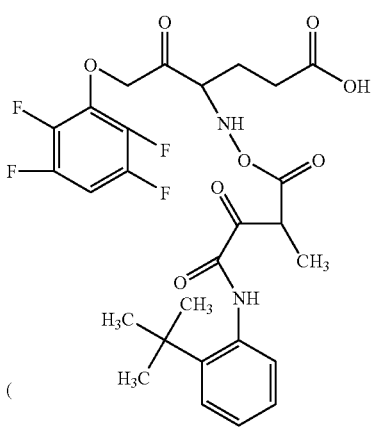

Yet another embodiment of the present invention comprises administering a compound of the present invention (e.g., represented by a structural formula selected from I-XXIII) in association with naphthoquinone, 2-methylnaphthoquinone, 2-hydroxynaphthoquinone, 5-hydroxynaphthoquinone, 5,8-dihydroxynaphthoquinone, alkannin or shikonin (Takeshita et al., Analytical Biochem. 247: 242-246 (1997)).

A further embodiment of the present invention comprises administering a compound of the present invention (e.g., represented by a structural formula selected from I-XXIII) in association with 1-amino-1,3,5-trimethylcyclohexane, 1-amino-1(trans),3(trans),5-trimethylcyclohexane, 1-amino-1(cis),3(cis),5-trimethylcyclohexane, 1-amino-1,3,3,5-tetramethylcyclohexane, 1-amino-1,3,3,5,5-pentamethylcyclohexane, 1-amino-1,3,5,5-tetramethyl-3-ethylcyclohexane, 1-amino-1,5,5-trimethyl-3,3-diethylcyclohexane, 1-amino-1,5,5-trimethyl-cis-3-ethylcyclohexane, 1-amino-(1S,5S)cis-3-ethyl-1,5,5-trimethylcyclohexane, 1-amino-1,5,5-trimethyl-trans-3-ethylcyclohexane, 1-amino-(1R,5S)trans-3-ethyl-1,5,5-trimethylcyclohexane, 1-amino-1-ethyl-3,3,5,5-tetramethylcyclohexane, 1-amino-1-propyl-3,3,5,5-tetramethylcyclohexane, N-methyl-1-amino-1,3,5,5-pentamethylcyclohexane, N-ethyl-1-amino-1,3,5,5-pentamethylcyclohexane, or N-(1,3,3,5,5-pentamethylcyclohexyl) pyrrolidine or any other 1-aminoalkylcyclohexane N-methyl-D-aspartate (NMDA) inhibitors disclosed in U.S. Pat. No. 6,034,134.

A further embodiment of the present invention comprises administering a compound of the present invention (e.g., represented by a structural formula selected from I-XXIII) in association with d-α-tocopherol or any other anti-HCV compound disclosed in U.S. Pat. No. 5,922,757.

Another embodiment of the present invention comprises administering a compound of the present invention (e.g., represented by a structural formula selected from I-XXIII) in association with tauroursodeoxycholic acid, chenodeoxycholic acid, ursodeoxycholic acid or free bile acid or any other bile acid HCV inhibitor disclosed in U.S. Pat. No. 5,846,964.

Another embodiment of the present invention comprises administering a compound of the present invention (e.g., represented by a structural formula selected from I-XXIII) in association with 1,1'-[1,4-phenylenebis (methylene)]bis(4,4'-trans-(4,5,6,7,8,9-hexahydro)benzimidazoyl)piperidine, 1,1'-[1,4-phenylenebis( methylene)]bis(4,4'-benzimidazoyl) piperidine or any other anti-HCV compound disclosed in U.S. Pat. No. 5,830,905.

Another embodiment of the present invention comprises administering a compound of the present invention (e.g., represented by a structural formula selected from I-XXIII) in association with N,N'-4-[(2-benzimidazole)phenyl]-1,4-butanedicarboxamide, N,N'-4-[(2-benzimidazole)phenyl]-1,6-hexanedicarboxamide, N,N'-4-[(2-benzimidazole)phenyl]-1,8-octanedicarboxamide, N,N'-4-[(2-benzimidazole)phenyl]-1,9-nonanedicarboxamide, N,N'-4-[(2-benzimidazole)phenyl]-1,10-decanedicarboxamide or N,N'-4-[(2-benzimidazole)phenyl]-1,4-butenedicarboxamide or any other carboxamide HCV inhibitor disclosed in U.S. Pat. No. 5,633,388.

Another embodiment of the present invention comprises administering a compound of the present invention (e.g., represented by a structural formula selected from I-XXIII) in association with any of the polyadenylic acid (5') derivatives disclosed in U.S. Pat. No. 5,496,546.

A further embodiment of the present invention comprises administering a compound of the present invention (e.g., represented by a structural formula selected from I-XXIII) in association with 2',3'-dideoxyinosine (U.S. Pat. No. 5,026,687).

An embodiment of the present invention comprises administering a compound of the present invention (e.g., represented by a structural formula selected from I-XXIII) in association with

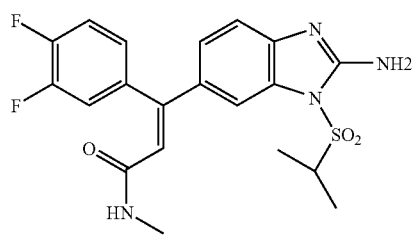

or any other benzimidazole disclosed in U.S. Pat. No. 5,891,874.

An additional embodiment of the invention comprises administering VX-950

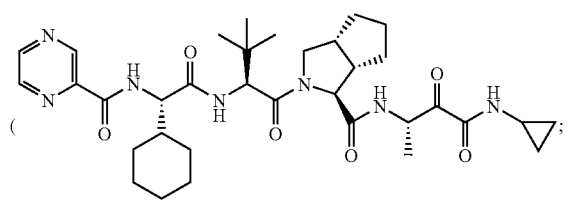

Lin et al., J. Biol. Chem. 279(17): 17508-17514 (2004)) in association with a compound of the present invention (e.g., represented by a structural formula selected from I-XXIII).

Another embodiment of the present invention comprises administering a compound of the present invention (e.g., represented by a structural formula selected from I-XXIII) in association with viramidine

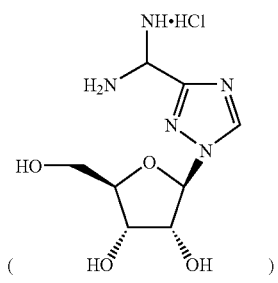

or levovirin

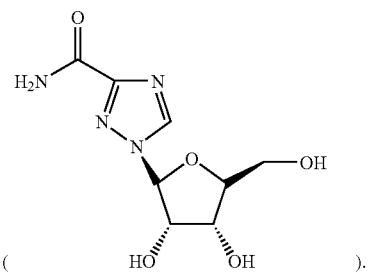
(              ).

Combinations of the invention include a compound of the present invention (e.g., represented by a structural formula selected from I-XXIII) "in association" with one or more additional anti-viral agents (e.g., ribavirin, interferon alfa-2a or 2b, or pegylated interferon alfa-2a or 2b). The term "in association" indicates that the components of the combinations of the invention can be formulated into a single composition for simultaneous delivery or formulated separately into two or more compositions (e.g., a kit). Furthermore, each component of a combination of the invention can be administered to a subject at a different time than when the other component is administered; for example, each administration may be given non-simultaneously (e.g., separately or sequentially) at several intervals over a given period of time. Moreover, the separate components may be administered to a subject by the same or by a different route (e.g., orally, intravenously, subcutaneously).

The present invention further comprises compositions comprising a compound of the present invention (e.g., represented by structural formula selected from I-XXIII) in association with one or more anti-viral agents discussed above (e.g., pegylated interferon alfa-2a or 2b or ribavirin) along with pharmaceutical compositions thereof.

Dosage and Administration

Typical protocols for the therapeutic administration of such substances are well known in the art. Pharmaceutical composition of the invention may be administered, for example, by any parenteral (e.g., subcutaneous injection, intramuscular injection, intravenous injection) or non-parenteral route (e.g., orally, nasally).

Pills and capsules of the invention can be administered orally. Injectable compositions can be administered with medical devices known in the art; for example, by injection with a hypodermic needle including the REDIPEN® or the NOVOLET® Novo Pen discussed above.

Injectable pharmaceutical compositions of the invention may also be administered with a needleless hypodermic injection device; such as the devices disclosed in U.S. Pat. Nos. 5,399,163; 5,383,851; 5,312,335; 5,064,413; 4,941,880; 4,790,824 or 4,596,556.

Compounds of the invention can be administered, for example, three times a day, twice a day, once a day, three times weekly, twice weekly or once weekly.

In an embodiment, the daily dose of a compound of the present invention (e.g., represented by a formula selected from I-XXIII) or of any other anti-viral agent administered in association with a compound of the invention (e.g., represented by a formula selected from I-XXIII) is, where possible, administered accordance with the *Physicians' Desk Reference* 2003 (*Physicians' Desk Reference*, 57th Ed); Medical Economics Company; ISBN: 1563634457; 57th edition (November 2002). The proper dosage can, however, be altered by a clinician to compensate for particular characteristics of the subject receiving the therapy depending, for example, on the potency of the compound administered, side-effects, age, weight, medical condition, overall health and response.

The term "therapeutically effective amount" means that amount of a therapeutic agent or substance (e.g., compound represented by structural formula selected from I-XXIII, interferon or ribavirin) that will elicit a biological or medical response of a tissue, system, subject or host that is being sought by the administrator (such as a researcher, doctor or veterinarian) which includes alleviation of the symptoms of Flaviviridae virus (e.g., HCV) infection and the prevention, slowing or halting of progression of Flaviviridae virus (e.g., HCV) infection and its symptom(s) to any degree including prevention of the infection of a host with a Flaviviridae virus (e.g., HCV) following transplant of a liver into said host. For example, in one embodiment, a "therapeutically effective dosage" of a compound of the invention (e.g., represented by a structural formula selected from I-XXIII) or a combination including another anti-viral agent (e.g., ribavirin and/or pegylated or unpegylated interferon alfa-2a or 2b) results in the eradication of detectable Flaviviridae Viral RNA (e.g., HCV RNA) for any period of time, for example, 12 or more weeks (e.g., 24 weeks). Detection of viral RNA in a host can be done easily using conventional well-known methods in the art. See also the Physicians' Desk Reference ("PDR") for the therapeutically effective dose and dosage regimens approved by the U.S. Federal Food and Drug Administration.

In an embodiment, a therapeutically effective dosage or amount of a compound represented by a structural formula selected from I-III is about 20 mg/day to about 800 mg per day; about 20 mg/day to about 600 mg per day; about 20 mg/day to about 400 mg per day; about 20 mg/day to about 100 mg per day; about 60 mg/day to about 800 mg per day; about 60 mg/day to about 600 mg per day; about 60 mg/day to about 400 mg per day; about 60 mg/day to about 200 mg per day; or about 60 mg/day to about 100 mg per day. For example, a compound of the invention (e.g., represented by a formula selected from I-III) can be administered in a dosage form containing from about 20 mg to about 800 mg of the compound (e.g., 20 mg, 50 mg, 100 mg, 200 mg, 400 mg, 600 mg or 800 mg).

In an embodiment, a therapeutically effective amount or dosage a compound represented by a structural formula of any of IV-XXIII is about 80 mg/day to about 1200 mg per day; about 80 mg/day to about 120 mg per day; about 80 mg/day to about 400 mg per day; about 80 mg/day to about 600 mg per day; or about 80 mg/day to about 1000 mg per day. For example, a compound of the invention (e.g., represented by a formula selected from IV-XXIII) can be administered in a dosage form containing from about 20 mg to about 1200 mg of the compound (e.g., 20 mg, 80 mg, 120 mg, 400 mg, 600 mg, 1000 mg or 1100 mg).

As discussed herein, methods of the present invention can include administering a compound comprising a structural formula selected from I-XXIII along with pegylated or unpegylated interferon alfa-2a, pegylated or unpegylated interferon alfa-2b, pegylated or unpegylated interferon alfa-2c, pegylated or unpegylated interferon alfa n-1, pegylated or unpegylated interferon alfa n-3, unpegylated pegylated consensus interferon, ribavirin or any combination thereof.

In an embodiment, a therapeutically effective dosage of interferon alfa-2b (e.g., INTRON-A®), particularly for the treatment of chronic hepatitis C is 3 million IU (international units) three times a week (TIW) administered subcutaneously or intramuscularly. In patients tolerating therapy with normalization of serum alanine aminotransferase (ALT) at 16 weeks of treatment, INTRON A® therapy should be extended to 18 to 24 months (72 to 96 weeks) at 3 million IU TIW to improve the sustained response rate.

If severe adverse reactions develop during INTRON A® treatment, the dose should be modified (50% reduction) or therapy should be discontinued as indicated below. If intolerance persists after dose adjustment, INTRON A® therapy should be discontinued.

In an embodiment, the recommended dose of PEG-interferon alfa-2b (e.g., PEG-INTRON®) regimen is from about 0.5 to about 1.5 µg/kg/week, preferably 1.0 µg/kg/week for one year.

In an embodiment, a therapeutically effective dosage of interferon alfa-2a (e.g., ROFERON-A®), particularly for the treatment of chronic hepatitis C, is 3 MIU three times a week (TIW) administered subcutaneously or intramuscularly for 12 months (48 to 52 weeks). As an alternative, patients may be treated with an induction dose of 6 MIU TIW for the first 3 months (12 weeks) followed by 3 MIU TIW for 9 months (36 weeks).

Patients who tolerate and partially or completely respond to therapy with ROFERON-A® but relapse following its discontinuation may be re-treated. Re-treatment with either 3 MIU TIW or with 6 MIU TIW for 6 to 12 months may be considered.

In an embodiment, a temporary dose reduction by 50% is recommended in patients who do not tolerate the prescribed dose of ROFERON-A®. If adverse events resolve, treatment with the original prescribed dose can be re-initiated. In patients who cannot tolerate the reduced dose, cessation of therapy, at least temporarily, is recommended.

In an embodiment, the recommended dose of PEG-interferon alfa-2a (e.g., PEGASYS®) monotherapy is 180 µg (1.0 mL) once weekly for 48 weeks by subcutaneous (SC) administration in the abdomen or thigh.

In an embodiment, a therapeutically effective dosage of consensus interferon alfa (e.g., INFERGEN®), particularly for treatment of chronic HCV infection, is 9 mcg TIW administered SC as a single injection for 24 weeks. At least 48 hours should elapse between doses of INFERGEN®).

In an embodiment, patients who tolerated previous interferon therapy and did not respond or relapsed following its discontinuation may be subsequently treated with 15 mcg of INFERGEN® TIW administered SC as a single injection for up to 48 weeks.

In an embodiment, for patients who experience a severe adverse reaction on INFERGEN®), dosage should be withheld temporarily. If the adverse reaction does not become tolerable, therapy should be discontinued. Dose reduction to 7.5 mcg may be necessary following an intolerable adverse event.

If adverse reactions continue to occur at the reduced dosage, the physician may discontinue treatment or reduce dosage further. However, decreased efficacy may result from continued treatment at dosages below 7.5 mcg.

During subsequent treatment for 48 weeks with 15 mcg of INFERGEN®, up to 36% of patients required dose reductions in 3 mcg increments.

In an embodiment, a therapeutically effective does of albumin-interferon-alpha (e.g., ALBUFERON®)) is about 120 mcg or about 180 mcg or about 240 mcg or about 320 mcg or about 400 mcg or about 500 mcg per day subcutaneously.

In an embodiment, a therapeutically effective dose of ribavirin (e.g., REBETROL®) depends on the patient's body weight. In an embodiment, the recommended dose of REBETOL® is provided, below, in Table 1.

TABLE 1

| Body weight | Recommended Dosing REBETOL Capsules |
|---|---|
| </=75 kg | 2 × 200-mg capsules AM, 3 × 200-mg capsules PM daily p.o. |
| >75 kg | 3 × 200 mg capsules AM, 3 × 200 mg capsules PM daily p.o. |

In an embodiment, the recommended duration of treatment with ribavirin (e.g., REBETOL®) for patients previously untreated with interferon is 24 to 48 weeks. The duration of treatment should be individualized to the patient depending on baseline disease characteristics, response to therapy, and tolerability of the regimen. After 24 weeks of treatment, virologic response should be assessed. Treatment discontinuation should be considered in any patient who has not achieved an HCV RNA below the limit of detection of the assay by 24 weeks.

In an embodiment, in patients who relapse following interferon therapy, the recommended duration of treatment with ribavirin (e.g., REBETOL®) is 24 weeks.

REBETOL® may be administered without regard to food, but should be administered in a consistent manner with respect to food intake.

In an embodiment, a combination of interferon alfa-2b and ribavirin (e.g., REBETRON®) is administered in association with a compound of the invention (e.g., represented by a formula selected from I-XXIII).

In an embodiment, the recommended duration of REBETRON® treatment for patients previously untreated with interferon is 24 to 48 weeks. The duration of treatment should be individualized to the patient depending on baseline disease characteristics, response to therapy, and tolerability of the regimen. After 24 weeks of treatment, virologic response should be assessed. Treatment discontinuation should be considered in any patient who has not achieved an HCV RNA below the limit of detection of the assay by 24 weeks. In patients who relapse following interferon therapy, the recommended duration of treatment is 24 weeks.

In an embodiment, the recommended dosage of a combination of ribavirin (e.g., REBETROL®)) and interferon alfa-2b (e.g., INTRON-A®) depends on patient body weigh. In an embodiment, the adult dosage regimen is set forth below in Table 2:

TABLE 2

| | Recommended Adult Dosing | |
|---|---|---|
| Body weight | REBETOL Capsules | INTRON A Injection |
| </=75 kg | 2 × 200-mg capsules AM, 3 × 200-mg capsules PM daily p.o. | 3 million IU 3 times weekly s.c. |
| >75 kg | 3 × 200-mg capsules AM, 3 × 200-mg capsules PM daily p.o. | 3 million IU 3 times weekly s.c. |

In an embodiment, the pediatric dosage regimen, for the combination, is set forth below in Table 3:

TABLE 3

Pediatric Dosing

| Body weight | REBETOL Capsules | INTRON A Injection |
|---|---|---|
| 25–36 kg | 1 × 200-mg capsule AM<br>1 × 200-mg capsule PM<br>daily p.o. | 3 million IU/m² 3 times<br>weekly s.c. |
| 37–49 kg | 1 × 200-mg capsule AM<br>2 × 200-mg capsules PM<br>daily p.o. | 3 million IU/m² 3 times<br>weekly s.c. |
| 50–61 kg | 2 × 200-mg capsules AM<br>2 × 200-mg capsules PM<br>daily p.o. | 3 million IU/m² 3 times<br>weekly s.c. |
| >61 kg | Refer to adult dosing table | Refer to adult dosing table |

In an embodiment, dosage modification of REBETOL®/INTRON-A® treatment is indicated when adverse reactions are observed in the patient. For example, in patients with a history of stable cardiovascular disease, a permanent dose reduction is required if the patient's hemoglobin decreases by >/=2 g/dL during any 4-week period. In addition, for these cardiac history patients, if the patient's hemoglobin remains <12 g/dL after 4 weeks on a reduced dose, the patient should discontinue combination REBETOL®/INTRON-A® therapy.

In an embodiment, it is recommended that a patient whose hemoglobin level falls below 10 g/dL have his/her REBETOL® dose reduced to 600 mg daily (1×200-mg capsule AM, 2×200-mg capsules PM). A patient whose hemoglobin level falls below 8.5 g/dL should be permanently discontinued from REBETOL®/INTRON A® therapy.

In an embodiment, when administered in combination with REBETOL®, the recommended dose of PEG-Intron® is 1.5 micrograms/kg/week. The recommended dose of REBETOL® is 800 mg/day in 2 divided doses: two capsules (400 mg) with breakfast and two capsules (400 mg) with dinner. REBETOL® should not be used in patients with creatinine clearance <50 mL/min.

Ideally, though not necessarily, an infected host who is administered a composition of the invention will, eventually, exhibit no detectable HCV RNA is his body for a period of time (e.g., 12 or more weeks).

The term "no detectable HCV-RNA" in the context of the present invention means that there is less than about 100 copies of HCV-RNA per ml of serum of the patient as measured by quantitative, multi-cycle reverse transcriptase PCR (rtPCT) methodology. Such PCR based assays are conventional and very well known in the art. In general, rtPCR is performed by isolating the RNA from a specimen, reverse-transcribing it to generate cDNAs, amplifying specific nucleic acid sequences by PCR, and then using a variety of methods to detect the amplified sequences (Urdea et al., Clin. Chem. 43:1507-1511 (1997)).

In one embodiment, a method of the present invention, when administered to a host infected with a Flaviviridae virus, will exhibit a sustained virologic response. The term "sustained virologic response" as used in the context of the present invention means that there is no detectable HCV-RNA in the serum of patients treated in accordance with the present invention for at least 24 weeks after the end of the combined therapy treatment. Preferably, the period of sustained virologic response is at least one year—or longer—after the end of treatment.

EXAMPLES

The following examples are intended to exemplify and further clarify what is the present invention and should not be construed to limit the present invention.

Example 1

Production of Ara-C-5'-stearylphosphate (III) and Ara-C-5'-stearylphosphate monosodium salt To 6.4 g (10 mmol) of $N^4$, $O^{2'}$, $O^{3'}$-triacetyl-Ara-C-5'-phosphate tri-n-butyl ammonium salt, 5 g of stearyl alcohol, 30 ml of pyridine and 8 g of p-toluenesulfonyl chloride were added and the mixture was maintained at 40° C. for 3 hours. Then, the reaction mixture was extracted after adding 50 ml of water and 50 ml of chloroform.

Deacetylation of the triacetyl compound in the chloroform solution was carried out by adding 20 ml of aqueous ammonia and ethanol thereto and the deacetylated compound was extracted with water.

After collecting the aqueous layer, the aqueous layer was adjusted to pH 2.5 by adding conc. hydrochloric acid, and the precipitated Ara-C-5'-stearylphosphate was collected by filtration. After adding 20 ml of water to the thus obtained precipitates and adjusting the solution to pH 10.5 by an aqueous 1 N solution of sodium hydroxide, 80 ml of ethanol were added to the solution. By collecting the generated precipitate through filtration, Ara-C-5'-stearylphosphate monosodium salt (α-type) was obtained in wet state, and by drying the wet material in the same manner as in Example 2, 4.20 g of Ara-C-5'-stearylphosphate monosodium salt (α-type) of m.p. 221° C. (decomposition) were obtained.

The purity of the thus obtained product was 99.62% by liquid chromatography and $E_1$ cm$^{1\%}$ (273 nm, 0.1N NaOH) was 151.4. This procedure is taken from U.S. Pat. No. 4,812,560.

Example 2

Production of Ara-C-5'-stearylphosphate monosodium salt

Into 1.5 liters of water 500 g of Ara-C-5'-stearylphosphate were added and after adjusting the pH of the mixture to 10.8 by sodium hydroxide while stirring the mixture, 6 liters of ethanol were added to the mixture. After allowing the mixture to cool for 16 hours, the thus formed precipitate was collected by centrifugation to obtain Ara-C-5'-stearylphosphate monosodium salt in wet state.

By drying the thus obtained wet salt at 30° C. under reduced pressure, 332 g of amorphous (α-type) Ara-C-5'-stearylphosphate monosodium salt of m.p. 223° C. (decomposition) were obtained.

The purity of the thus obtained product was 99.5% according to liquid chromatography and $E_1$ cm$^{1\%}$ (273 nm, 0.1N NaOH) was 152. 3.

The same result as above was obtained when acetone, methyl ethyl ketone, tetrahydrofurane or dioxane was added instead of ethanol to precipitate the monosodium salt. This procedure is taken from U.S. Pat. No. 4,812,560.

Example 3

Production of Ara-C-5'-stearylphosphate monosodium Salt

To 2.40 g of Ara-C-5'-stearylphosphate (a dried material), 6 ml of water were added and, after adjusting the mixture to pH 12.0 with aqueous 1N solution of sodium hydroxide, 30 ml of ethanol were added to the mixture and the mixture was stirred for 3 hours at 55° C. After cooling the mixture for 16 hours by standing, the precipitate was collected by filtration and dried for 10 hours at 30° C. under a reduced pressure to obtain 1.83 g of Ara-C-5'-stearylphosphate monosodium salt (α-type) of m.p. 220° C. (decomposition). The purity of the thus obtained product was 99.5% according to liquid chromatography and $E_1$ cm$^{1\%}$ (273 nim, 0.1N NaOH) was 150.9. This procedure is taken from U.S. Pat. No. 4,812,560.

Example 4

Production of Ara-C-5'-stearylphosphate monosodium salt

To 2.40 g of Ara-C-5'-stearylphosphate, 10 ml of water were added and, after adjusting the mixture to pH 10.0 by sodium hydroxide while stirring, the mixture, the thus formed solution was condensed to dryness under a reduced pressure to obtain 2.30 g of Ara-C-5'-stearylphosphate monosodium salt (α-type).

The melting point of the thus obtained product was 219.8° C. (decomposition), the purity thereof was 99.1% by liquid chromatography and $E_1$ cm$^{1\%}$ (273 nm, 0.1N NaOH) was 152.6. This procedure is taken from U.S. Pat. No. 4,812,560.

Example 5

Ara-C-5'-stearylphosphate monosodium salt monohydrate

To 10 g of Ara-C-5'-stearylphosphate, 30 ml of water were added and, after adjusting the pH of the mixture to 10.5 by 5N sodium hydroxide, 50 ml of ethanol were added to the thus formed solution with stirring at about 40° C. to precipitate the monosodium salt.

The mixture was heated to 65° C. and after adding the seed crystal of Ara-C-5'-stearylphosphate monosodium salt monohydrate (β-type), the mixture was maintained with stirring while keeping the temperature for 5 hours to form crystals. After microscopically confirming the completion of crystallization, 20 ml of ethanol were added to the mixture and the mixture was gradually cooled.

After one night, the crystals were filtrated and by drying under a reduced pressure 8.9 g of Ara-C-5'-stearylphosphate monosodium salt monohydrate (crystals of β-type) of m.p. 220° C. (decomposition) were obtained.

The purity of the thus obtained product was 99.7% by liquid chromatography and $E_1$ cm$^{1\%}$ (273 nm, 0.1N NaOH) was 153.0. This procedure is taken from U.S. Pat. No. 4,812,560.

Example 6

Synthesis of $N^4$-[(Dimethylamino)methylene]arabinocytidine (VI)

Ara-C (300 mg, 1.23 mmol) in DMF (5 mL) was reacted with dimethylformamide dimethyl acetal (1.7 g, 14.2 mmol). On evaporation and crystallization from a minimum amount of ethanol, white crystals of $N^4$-[(Dimethylamino)methylene]arabinocytidine were obtained (371 mg, 100%).

This procedure is taken from Kerr et al., J. Pharm. Sci. 83(4): 582-586 (1994).

Example 7

Synthesis of $N^4$-[(Diethylamino)methylene]arabinocytidine (VI)

Ara-C (500 mg, 2.05 mmol) in DMF (2 mL) was reacted with diethylformamide dimethyl acetal (2.16 g, 14.7 mmol). After evaporation, the recrystallization of the residue from a variety of solvents proved difficult. The residue was finally crystallized from a solution of 4% MeOH in $CH_2Cl_2$, to give $N^4$-[(Diethylamino)methylene]arabinocytidine as fine colorless, whitish crystals (601 mg, 90%).

This procedure is taken from Kerr et al., J. Pharm. Sci. 83(4): 582-586 (1994).

Example 8

Synthesis of $N^4$-[(Dipropylamino)methylene]arabinocytidine (VIII)

Ara-C (85 mg, 0.35 mmol) in DMF (2 mL) was reacted with dipropylformamide dimethyl acetal (0.9 g, 5.14 mmol). Evaporation and crystallization from ethanol-ethyl acetate gave $N^4$-[(Dipropylamino)methylene]arabinocytidine (104 mg, 85%).

This procedure is taken from Kerr et al., J. Pharm. Sci. 83(4): 582-586 (1994).

Example 9

Synthesis of $N^4$-[(Dibutylamino)methylene]arabinocytidine (IX)

Ara-C (85 mg, 0.35 mmol) in DMF (2 mL) is reacted with dibutylformamide dimethyl acetal (0.9 g, 5.14 mmol). Evaporation and crystallization from ethanol-ethyl acetate gave $N^4$-[(Dibutylamino)methylene]arabinocytidine (104 mg, 85%).

Example 10

Synthesis of $N^4$-[(Diisopropylamino)methylene]arabinocytidine (X)

Ara-C (500 mg, 2.05 mmol) in DMF (10 mL) was reacted with diisopropylformamide dimethyl acetal (2.3 g, 13.2 mmol). After evaporation, the residue was crystallized from ethanol-ether to give pale lemon-colored crystals of $N^4$-[(Diisopropylamino)methylene]arabinocytidine (723 mg, 93%).

This procedure is taken from Kerr et al., J. Pharm. Sci. 83(4): 582-586 (1994).

Example 11

Synthesis of $N^4$-[Piperidinomethylene]arabinocytidine (XI)

Ara-C (500 mg, 2.05 mmol) in DMF (10 mL) was reacted with N-(dimethoxy methyl)piperidine (2.7 g, 16.8 mmol) for several hours at room temperature. The contents were evaporated and the residue chromoatographed over silica gel using 1-6% MeOH in $CH_2Cl_2$. The desired fractions were collected and evaporated. The foam obtained was recrystallized from a mixture of ethanol, $CH_2Cl_2$, and ethyl acetate to give $N^4$-[Piperidinomethylene]arabinocytidine (594 mg, 85%).

This procedure is taken from Kerr et al., J. Pharm. Sci. 83(4): 582-586 (1994).

Example 12

Synthesis of N$^4$-[Morpholinomethylene]arabinocytidine (XII)

Ara-C (100 mg, 0.41 mmol) in DMF (5 mL) was reacted with N-(dimethoxymethyl)morpholine (1.35 g, 9.3 mmol). Evaporation and subsequent crystallization from ethyl acetate-ether gave N$^4$-[Morpholinomethylene]arabinocytidine (130 mg, 93%).

This procedure is taken from Kerr et al., J. Pharm. Sci. 83(4): 582-586 (1994).

Example 13

Synthesis of N$^4$-[Pyrrolidinomethylene]arabinocytidine (XIII)

Ara-C (100 mg, 0.41 mmol) in DMF (5 mL) was reacted with N-(dimethoxymethyl)pyrrolidine (0.9 g, 6.2 mmol). Evaporation and subsequent crystallization from ethyl acetate-ether gave N$^4$-[Pyrrolidinomethylene]arabinocytidine (119 mg, 89%).

This procedure is taken from Kerr et al., J. Pharm. Sci. 83(4): 582-586 (1994).

Example 14

Synthesis of N$^4$-[Dimethylpiperidinomethylene]arabinocytidine (XIV)

Ara-C (500 mg, 2.05 mmol) in DMF (10 mL) is reacted with N-(dimethoxy methyl)dimethyl piperidine (2.7 g, 16.8 mmol) for several hours at room temperature. The contents are evaporated and the residue chromatographed over silica gel using 1-6% MeOH in $CH_2Cl_2$. The desired fractions are collected and evaporated. The foam obtained is recrystallized from a mixture of ethanol, $CH_2Cl_2$, and ethyl acetate to give N$^4$-[Dimethylpiperidinomethylene]arabinocytidine.

Example 15

Dose Response and Cell Toxicity Assay

This example demonstrates the ability of various compounds of the invention to inhibit the ability of cells to maintain and replicate a replicon. The example also evaluates the toxicity level of the various compounds on the cells.

Cell Culture. Cells of the luciferase replicon cell line (Vrolijk et al., J. Virol. Methods 110:201-209 (2003)) was grown in Dulbecco's minimal essential medium (DMEM) supplemented with 2 mM glutamine, non-essential amino acids (NEAA), 10 mM HEPES, 0.075% sodium bicarbonate, 100 U/ml penicillin and 100 µg/mL streptomycin, and 10% fetal bovine serum. To maintain the selection for replicon, 0.3 mg/mL of G418 were added to the culture media.

Dose-Response and Luciferase Assays. Replicon cells were seeded at 5000 cells/well in 96-well collagen I-coated Biocoat plates (Becton Dickinson; Palo Alto, Calif.). Twenty-four hrs post-seeding, compounds (see Table 1 below) were added to replicon cells. The final concentration of DMSO was 0.5%, fetal bovine serum was 10%, and G418 was not added. The cells were incubated with the compounds for 2 days, at which point the cells were washed with PBS and lysed in 40 µl Glo Lysis Buffer (Promega; Madison, Wis.). 20 µl of lysates were mixed with 100 µl Luciferase Assay Reagent (Promega) and read on a Microtiter Plate Luminometer MLX (DYNEX Technologies; Chantilly, Va.). The fold of reduction in luciferase signal compared to no compound control was plotted against drug concentration and fitted to the sigmoid dose response model using PRISM software (Graphpad Software Inc.; San Diego, Calif.).

Taqman Assay Method. Replicon cells were seeded at 4000 cells/well in 96-well collagen l-coated Biocoat Plates (Becton Dickinson). Twenty-four hours post-seeding, compounds were added to replicon cells. The final concentration of DMSO was 0.5%, fetal bovine serum was 10%, and no G418 was added. Cells were incubated with compounds for 2 days, at which point the cells were washed with PBS and lysed in 1X cell lysis buffer (Ambion). The replicon RNA level was measured using real time PCR (Taqman assay). The amplicon was located in NS5B. The PCR primers were 5B.2F, ATGGACAGGCGCCCTGA (SEQ ID NO: 1); 5B.2R, TTGATGGGCAGCTTGGTTTC (SEQ ID NO: 2); the probe sequence was FAM-labeled CACGCCATGCGCTGCGG (SEQ ID NO: 3). GADPH RNA was used as an endogenous control and was amplified in the same reaction as NS5B (multiplex PCR) using primers and VIC-labeled probe recommended by the manufacturer (PE Applied Biosystem). The real-time RT-PCR reactions were run on the ABI PRISM 7900HT Sequence Detection System using the following program: 48° C for 30 minutes, 95° for 10 minutes, 40 cycles of 95° for 15 seconds, 60° for 1 minute. The ΔCT values ($CT_{58}CT_{GADPH}$) were plotted against drug concentration and fitted to the sigmoid dose response model using SAS system (SAS Institute, Inc.) or PRISM software (Graphpad Software, Inc.). IC50 was the drug dose response necessary to achieve an increase of 1in ΔCT over the projected baseline. IC90 was the drug dose response necessary to achieve an increase of 3.2 over the baseline. All Taqman reagents were from PE Applied Biosystem.

Cell toxicity assay. The toxicity of compounds on the replicon cells were measured by MTS assay following manufacturer's instructions (Promega). Briefly, 20 µl of CellTiter 96®AQueous One Solution Reagent were added to each well of the 96-well plate containing 100 µl of culture medium. The plates were incubated for 30-60 minutes before reading OD by DYNEX MRX.

TABLE 4

Dose response and cell-toxicity assay results.

| Compound | IC50 (µM) | IC90 | EC50 | EC90 | CC50 | TI |
|---|---|---|---|---|---|---|
| X | >10 | >10 | 0.03 | 2 | >10 | >300 |
| XI | >10 | >10 | 0.07 | 8 | >10 | >100 |
| XII | >10 | >10 | 0.02 | 1.5 | >10 | >500 |
| XIII | >10 | >10 | 0.09 | 5 | >10 | >100 |
| Cytarabine | ~10 | >10 | 0.05 | 4 | >10 | >200 |
| Ribavirin | 40–100 | not reached | 20 | 80 | ~500 | ~25 |

IC50: drug dose necessary to reach a 2-fold decrease in replicon RNA level.

IC90: drug dose necessary to reach a 10-fold decrease in replicon RNA level

EC50: drug dose necessary to reach a 2-fold decrease in luciferase signal.

EC90: drug dose necessary to reach a 10-fold reduction in luciferase signal.

CC50: drug dose necessary to reduce the MTS signal to 50% of that of no drug control TI:CC50/EC50 in 5-2 cells.

All units are µM.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

ing group, wherein $R^5$ is —OH, a straight or branched chain $C_9$ to $C_{24}$ alkylphosphate or a straight or branched chain $C_9$ to $C_{24}$ alkenylphosphate group or a pharmaceutically acceptable leaving group and wherein $R^1$ and $R^2$ are independently $C_1$ to

---

---

What is claimed is:

1. A method for treating an infection by a virus which is a member of the Flaviviridae family of viruses, in a mammalian host, comprising administering to said host a therapeutically effective amount of a compound represented by structural formula IV

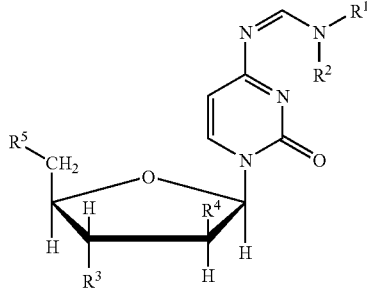

IV or a pharmaceutically acceptable salt thereof or a pharmaceutical composition thereof which composition comprises a pharmaceutically acceptable carrier; wherein $R^3$ and $R^4$ are independently —OH or a pharmaceutically acceptable leaving group, wherein $R^5$ is —OH, a straight or branched chain $C_9$ to $C_{24}$ alkylphosphate or a straight or branched chain $C_9$ to $C_{24}$ alkenylphosphate group or a pharmaceutically acceptable leaving group and wherein $R^1$ and $R^2$ are independently $C_1$ to $C_{10}$ alkyl or wherein $R^1$ and $R^2$ taken together with N form a $C_3$ to $C_7$ ring represented by the following structural formula:

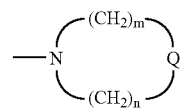

wherein n and m are independently 0, 1, 2 or 3 and Q is $CH_2$, NR, O, S, SO or $SO_2$; and R is independently H, $C_1$ to $C_6$ alkyl or $C_1$ to $C_6$ acyl or wherein $R^1$ and $R^2$, taken together with the N, are represented by the structural formula:

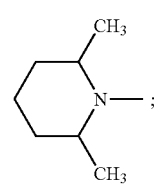

and wherein said pharmaceutically acceptable leaving groups groups are capable of being converted to —OH, -phosphate, —F or —CH₃ when the compound of structural formula IV is administered in vivo and are independently represented by structural formula

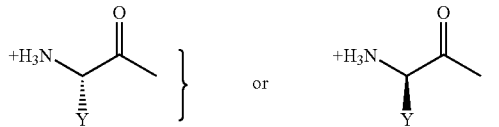

or

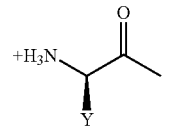

wherein Y=H, CH₃, CH₃CH₂—, CH₃CH₂CH₂—, Me₂CH—, Me₂CH₂CH₂—, CH₃CH₂CH(Me)—, PhCH₂—, HOOCCH₂CH₂—, HSCH₂—, HOOCCH₂—, MeSCH₂CH₂—, HOCH₂—,

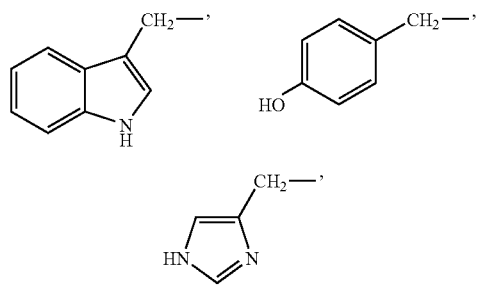

H₂N(CH₂)₄—, or CH₃CH(OH)—, or a pharmaceutically acceptable salt thereof, or Y, taken together with the alpha-carbon and N, form

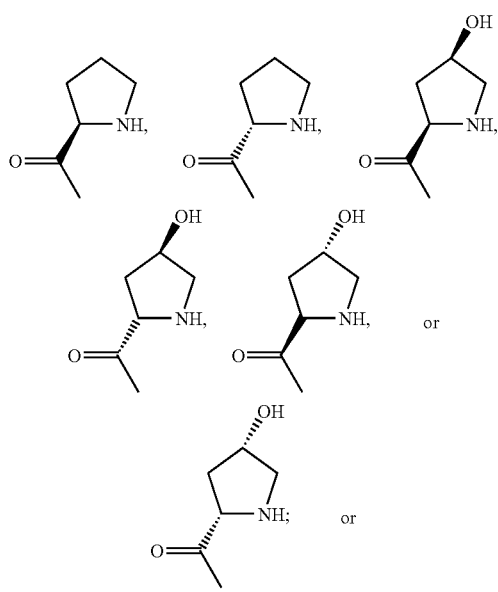

wherein the pharmaceutically acceptable leaving groups are capable of being converted to —OH, -phosphate, —F or —CH₃ when the compound of structural formula IV is administered in vivo and are independently represented by a structural formula selected from the group consisting of:

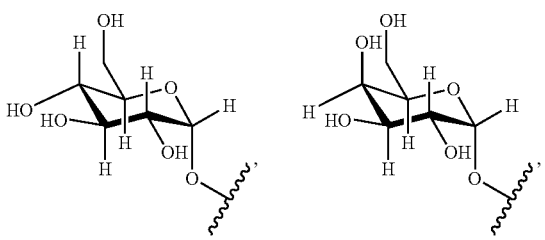

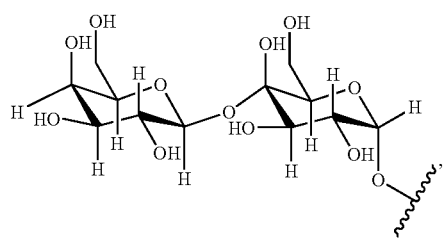

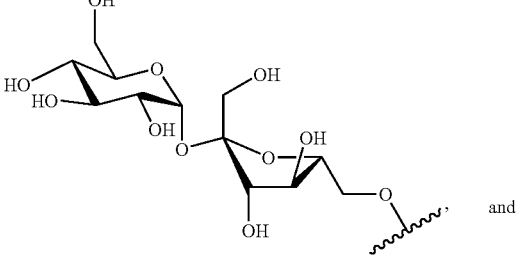

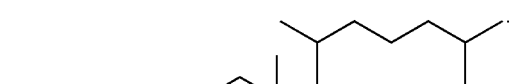

and

2. The method claim 1 wherein the virus is hepatitis C virus.

3. The method of claim 1, wherein the compound represented by formula IV is administered in association with interferon-alfa, pegylated interferon-alfa or albumin-interferon-alpha.

4. The method of claim 1 wherein the compound represented by formula IV is administered in association with an interferon-alfa selected from the group consisting of interferon alfa-2a, interferon alfa-2b, interferon alfa-2c, interferon alfa n-1, interferon alfa n-3 and consensus interferon.

5. The method of claim 1 wherein the compound represented by formula IV is administered in association with a pegylated interferon-alfa selected from the group consisting of pegylated interferon alfa-2a, pegylated interferon alfa-2b, pegylated interferon alfa-2c, pegylated interferon alfa n-1, pegylated interferon alfa n-3, and pegylated consensus interferon.

6. The method of claim 1, wherein the compound represented by formula IV is administered in association with ribavirin.

7. The method of claim 1 wherein $R^5=$

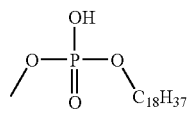

or a corresponding ion thereof.

8. The method of claim 1 wherein $R^3=R^4=R^5=-OH$.

9. The method of claim 1, wherein $R^1$ and $R^2$ are $C_1$-$C_5$ alkyl.

10. The method of claim 9, wherein $R^1$ and $R^2$ are isopropyl.

11. The method of claim 1, wherein $R^1$ and $R^2$ taken together with N are represented by the structural formula:

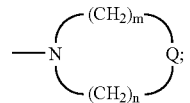

wherein n and m are independently 0, 1, 2 or 3 and Q is $CH_2$, NR, O, S, SO or $SO_2$; and R is independently H, $C_1$ to $C_6$ alkyl or $C_1$ to $C_6$ acyl.

12. The method of claim 1, wherein $R^1$ and $R^2$ taken together with N are represented by the following structural formula:

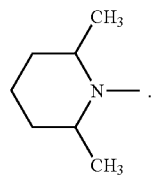

13. The method of claim 1 wherein the host is administered the compound represented by structural formula IV following transplantation of a liver into said host or transfusion of blood into said host.

14. A method for treating an infection by a virus which is a member of the Flaviviridae family of viruses, in a mammalian host, comprising administering to said host a therapeutically effective amount of a compound represented by a structural formula selected from the group consisting of:

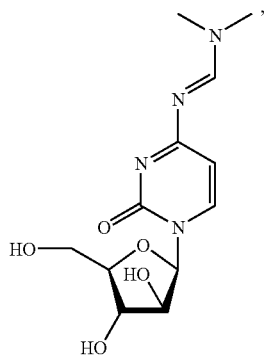

VI

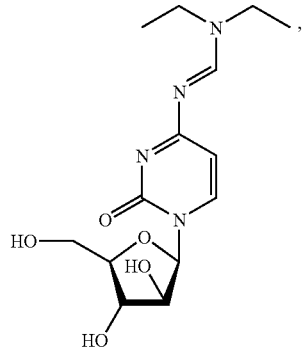

VII

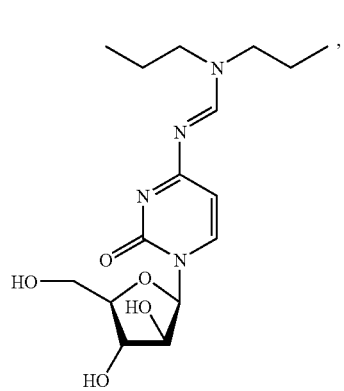

VIII

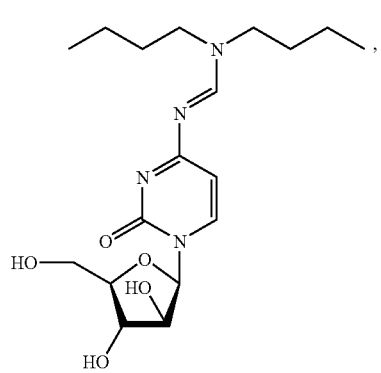

IX

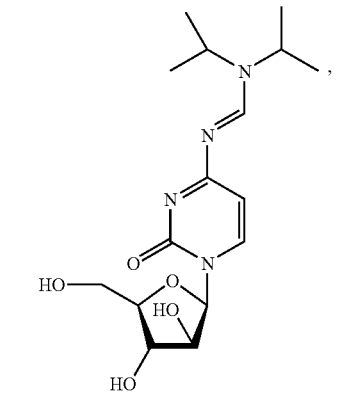

X

-continued
XI
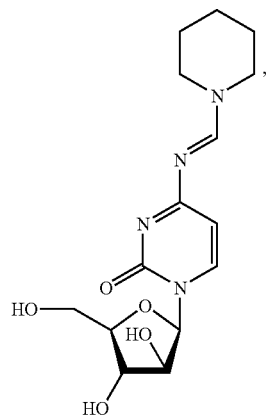
XII
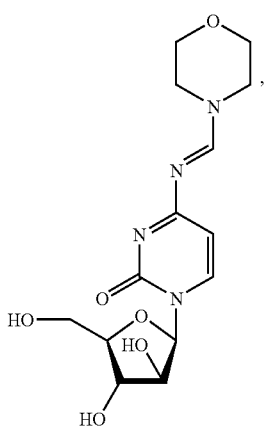
XIII
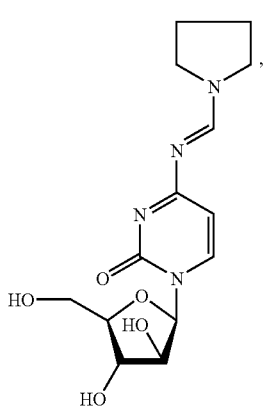
-continued
XIV
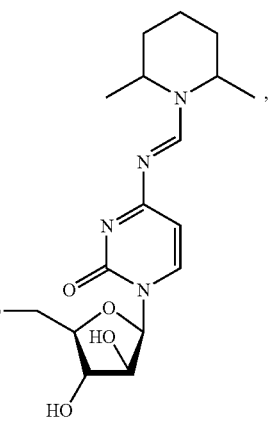
XV
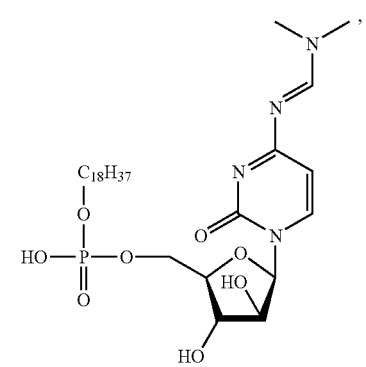
XVI
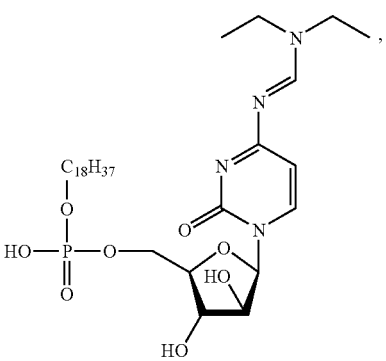
XVII
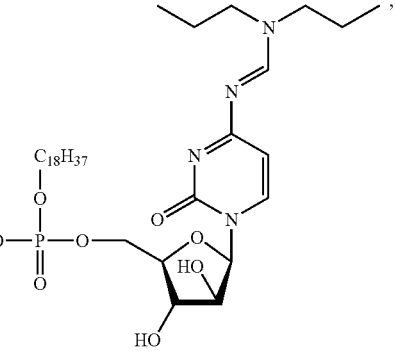

-continued

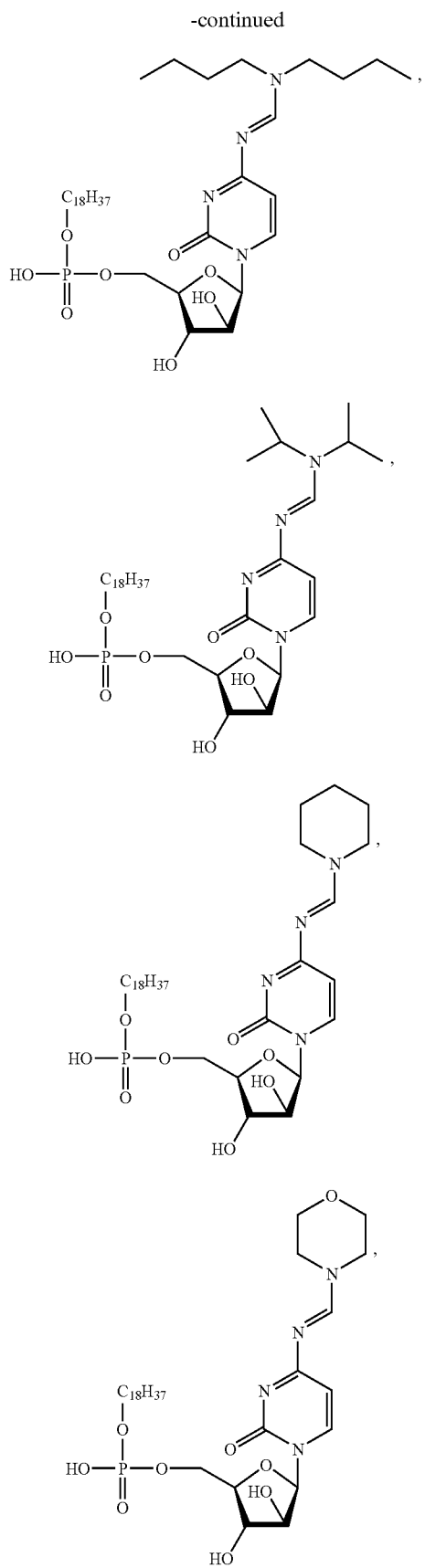

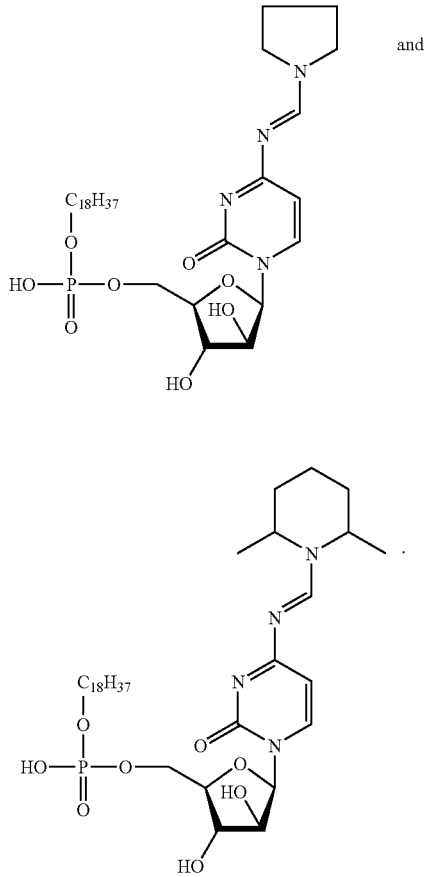

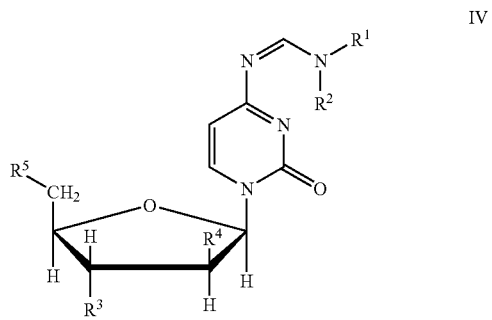

15. A composition represented by structural formula IV $$\text{IV}$$

or a pharmaceutically acceptable salt thereof or a pharmaceutical composition thereof which composition comprises a pharmaceutically acceptable carrier; wherein $R^3$ and $R^4$ are independently —OH or a pharmaceutically acceptable leaving group, wherein $R^5$ is a straight or branched chain $C_9$ to $C_{24}$ alkylphosphate or a straight or branched chain $C_9$ to $C_{24}$ alkenylphosphate group and wherein $R^1$ and $R^2$ are independently $C_1$ to $C_{10}$ alkyl or wherein $R^1$ and $R^2$ taken together with N form a $C_3$ to $C_7$ ring represented by the following structural formula:

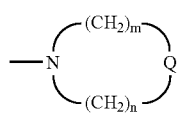

wherein n and m are independently 0, 1, 2 or 3 and Q is $CH_2$, NR, O, S, SO or $SO_2$; and R is independently H, $C_1$ to $C_6$ alkyl or $C_1$ to $C_6$ acyl or wherein $R^1$ and $R^2$, taken together with the N, are represented by the structural formula:

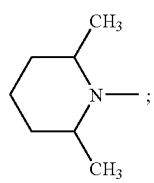

and wherein said pharmaceutically acceptable leaving groups are capable of being converted to —OH, -phosphate, —F or —$CH_3$ when the compound of structural formula IV is administered in vivo and are independently represented by the structural formula

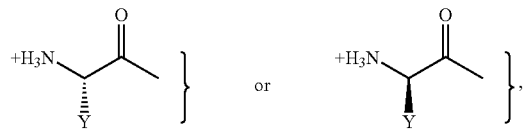

wherein Y=H, $CH_3$, $CH_3CH_2$—, $CH_3CH_2CH_2$—, $Me_2CH$—, $Me_2CH_2CH_2$—, $CH_3CH_2CH(Me)$—, $PhCH_2$—, $HOOCCH_2CH_2$—, $HSCH_2$—, $HOOCCH_2$—, $MeSCH_2CH_2$—, $HOCH_2$—

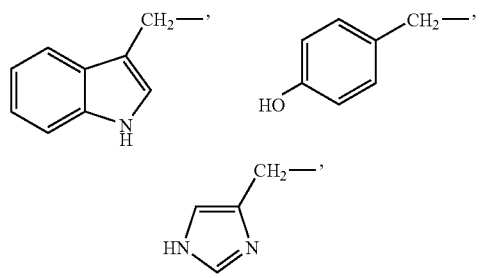

$H_2N(CH_2)_4$—, or $CH_3CH(OH)$—, or a pharmaceutically acceptable salt thereof, or Y, taken together with the alpha-carbon and N, form

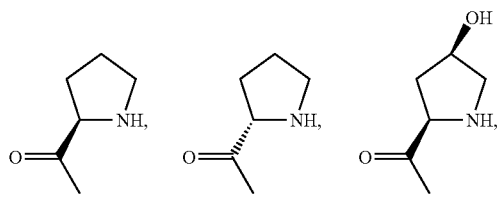

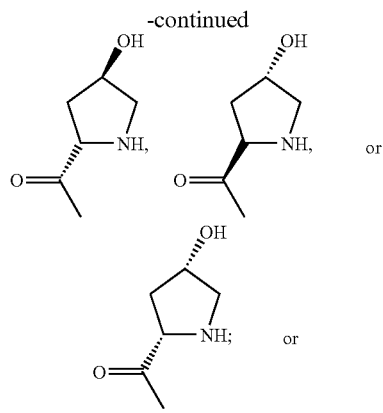

or wherein said pharmaceutically acceptable leaving groups are capable of being converted to —OH, -phosphate, —F or —$CH_3$ when the compound of structural formula IV is administered in vivo and are independently represented by a structural formula selected from the group consisting of:

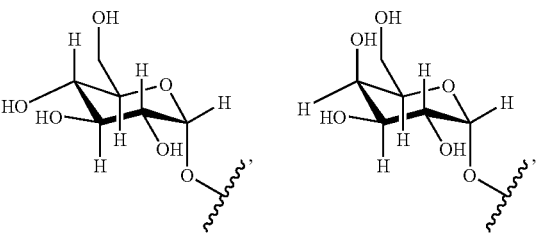

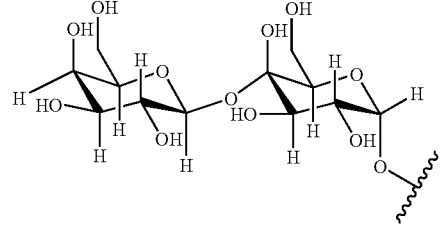

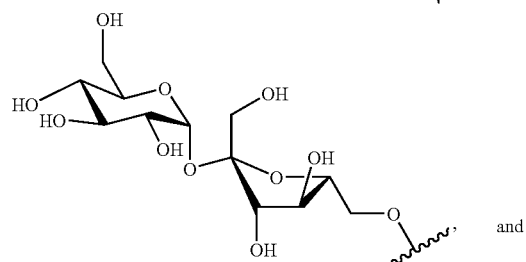

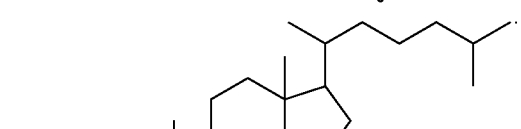

16. A composition which is represented by a structural formula selected from the group consisting of:

-continued
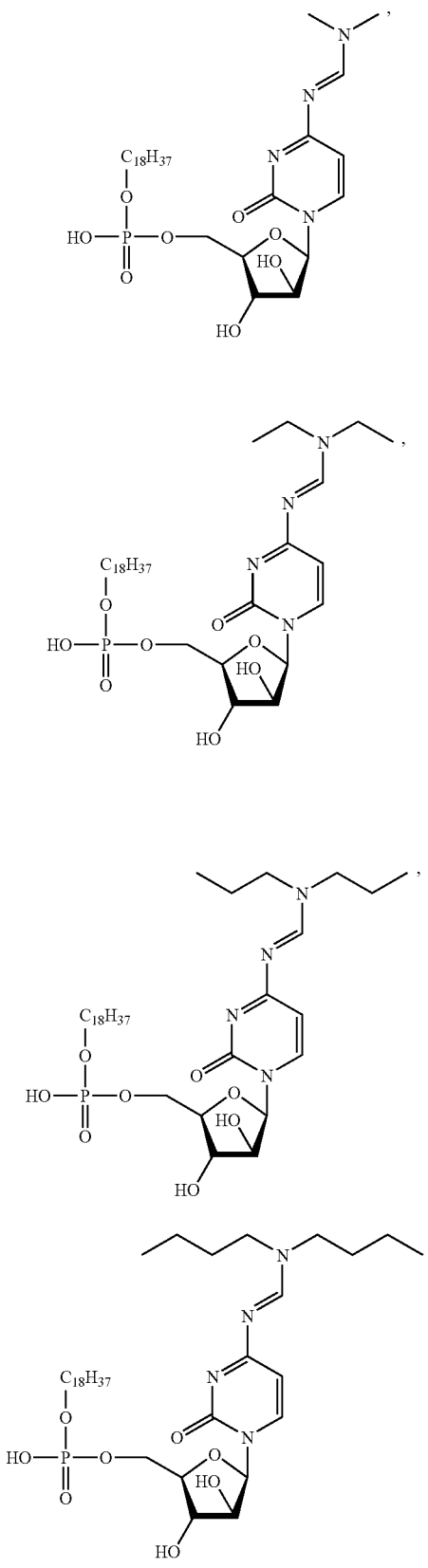
XV
XVI
XVII
XVIII
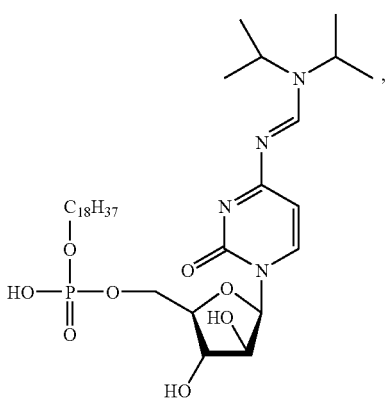
XIX
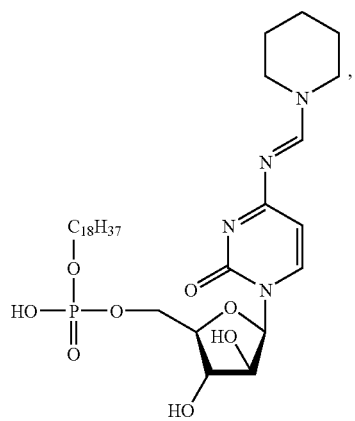
XX
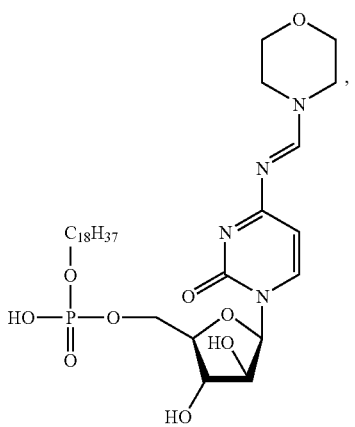
XXI
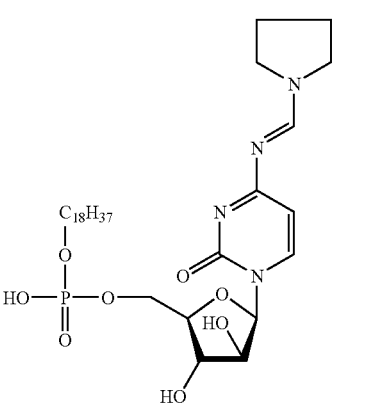
XXII
and

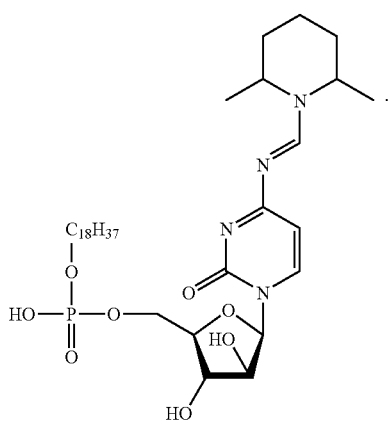

XXIII

17. The method of claim 1 wherein the subject is human.
18. The method of claim 14 wherein the subject is human.
19. The method of claim 14 wherein the compound is administered in association with interferon alfa-2b.
20. The method of claim 14 wherein the compound is administered in association with interferon alfa-2a.
21. The method of claim 14 wherein the compound is administered in association with pegylated interferon alfa-2b.
22. The method of claim 14 wherein the compound is administered in association with pegylated interferon alfa-2a.
23. The method of claim 14 wherein the compound is administered in association with ribavirin.
24. The method of claim 14 wherein the compound is administered in association with ribavirin and interferon alfa-2b.
25. The method of claim 17 wherein the virus is hepatitis C virus.
26. The method of claim 18 wherein the virus is hepatitis C virus.

* * * * *